United States Patent

Dahmen et al.

[11] Patent Number: 5,858,920
[45] Date of Patent: Jan. 12, 1999

[54] SELECTIVE HERBICIDES BASED ON HETEROARYLOXY-ACETAMIDES E.G., FLUTHIAMIDE

[75] Inventors: Peter Dahmen, Neuss; Rolf Deege, Monheim; Heinz Förster, Kadenbach; Hans-Jochem Riebel, Wuppertal; Johannes-Rudolf Jansen, Monheim, all of Germany

[73] Assignee: Bayer Aktiengesellschaft, Leverkusen, Germany

[21] Appl. No.: 897,188

[22] Filed: Jul. 21, 1997

Related U.S. Application Data

[62] Division of Ser. No. 573,804, Dec. 18, 1995, abandoned.

[30] Foreign Application Priority Data

Dec. 23, 1994 [DE] Germany .................. 44 46 341.3

[51] Int. Cl.$^6$ ................ A01N 25/32; A01N 43/824; A01N 43/653; A01N 43/90
[52] U.S. Cl. .............. 504/103; 504/106; 504/108; 504/112; 504/130; 504/136; 504/139
[58] Field of Search ................... 504/106, 108, 504/112, 130, 136, 139, 103

[56] References Cited

U.S. PATENT DOCUMENTS

| | | | |
|---|---|---|---|
| 4,988,380 | 1/1991 | Forster et al. | 71/90 |
| 5,502,025 | 3/1996 | Bussler | 504/107 |
| 5,593,942 | 1/1997 | Santel et al. | 504/134 |

FOREIGN PATENT DOCUMENTS

| | | |
|---|---|---|
| 3418167 | 11/1985 | Germany . |
| 9402014 | 2/1994 | WIPO . |

OTHER PUBLICATIONS

Hopkins, William L. Global Herbicide Directory, 1st Ed. "Eclipse, Uptake, metosulam, DE–511". Ag Chem Information Services: Indianapolis, Indiana. p. 48, 1994.

*Primary Examiner*—S. Mark Clardy
*Attorney, Agent, or Firm*—Sprung Kramer Schaefer & Briscoe

[57] ABSTRACT

Novel herbicidal active compound combinations consisting of (a) a heteroaryloxy-acetamide of the formula (I)

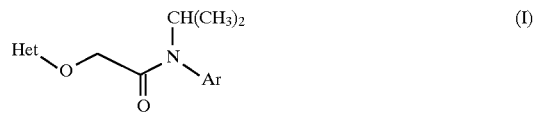

in which
Het represents thiadiazolyl which is substituted by halogen or by $C_1$-$C_4$-alkyl or phenyl, each of which is optionally substituted by halogen, and
Ar represents phenyl which is optionally substituted by halogen, $C_1$-$C_4$-alkyl or $C_1$-$C_4$-halogenoalkyl, and (b) one or more compounds from a second group of herbicides (according to the description) and/or a compound which improves the tolerance by crop plants (according to the description) exhibit, at certain weight ratios, synergistic effects and/or particularly good tolerance by crop plants with high herbicidal activity.

9 Claims, No Drawings

SELECTIVE HERBICIDES BASED ON HETEROARYLOXY-ACETAMIDES E.G., FLUTHIAMIDE

This application is a division, of application Ser. No. 08/573,804, filed Dec. 18, 1995, abandoned.

The invention relates to novel selective-herbicidal, synergistic active compound combinations which consist on the one hand of known heteroaryloxy-acetamides and on the other hand of known, herbicidally active compounds and/or compounds which improve the tolerance by crop plants, which combinations can be used with particular success for the selective combating of weeds in a variety of crop cultures.

Heteroaryloxyacetamides are, as strong herbicides which are particularly active against monocotyledon weeds, the subject of a range of patent applications (cf. EP-A 5501, EP-A 18497, EP-A 29171, EP-A 94514, EP-A 100044, EP-A 100045, EP-A 161602, EP-A 195237, EP-A 348734, EP-A 348737, DE-A 4317323). The action of these compounds and/or their tolerance by crop plants, however, are not always entirely satisfactory.

Disclosures have also been made of active compound combinations comprising heteroaryloxy-acetamides and other herbicidally active compounds for achieving a synergistic effect (cf. WO-A 94/02014) and/or of heteroaryloxy-acetamides and compounds which are able to improve the tolerance of herbicides by crop plants (cf. DE-A 3418167). With these combination products too, however, the application properties are not entirely satisfactory.

Surprisingly it has now been found that a series of known active compounds from the class of the heteroaryloxy-acetamides, when used in conjunction with known herbicidally active compounds from a variety of classes of substance and/or compounds which improve the tolerance by crop plants, exhibit outstandingly synergistic effects in respect of their action against weeds and/or significantly improve the tolerance by crop plants, and can be used with particular advantage as broadly effective combination preparations for selective combating of weeds in crop cultures, for example in maize.

The invention relates to selective-herbicidal compositions, characterized by an effective content of an active compound combination consisting of (a) a heteroaryloxy-acetamide of the general formula (I)

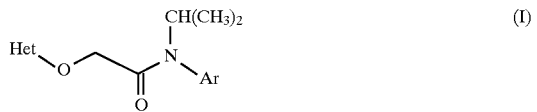

in which

Het represents thiadiazolyl which is substituted by halogen or by $C_1$–$C_4$-alkyl or phenyl, each of which is optionally substituted by halogen, and Ar represents phenyl which is optionally substituted by halogen, $C_1$–$C_4$-alkyl or $_1$–$C_4$-halogenoalkyl, ("active compounds of group 1") and (b) one or more compounds from a second group of herbicides which contains the active compounds mentioned below: N-(4,6dimethoxy-pyrimidin-2-yl-N'-(3-chloro-4-methoxycarbonyl-1-methyl-pyrazol-5-1-yl-sulfonyl-urea (clopyrasulfuron, halosulfuron, NC-319), 2-chloro-N-(2,4-dimethyl-3-thienyl)-N-(2-methoxy-1-methyl-ethyl)-acetamide (dimethenamid, SAN-582), 2-chloro-N-(2,6dimethyl-phenyl)-N-(1H-pyrazol-1-yl-methyl)-acetamide (metazachlor), N-(4,6-dimethoxy-pyrimidin-2-yl-N'-(3-ethylsulfonyl-pyridin-2-yl-sulfonyl-urea (rimsulfuron), 3-i-propyl-1H-2,1,3-benzothiadiazin-4(3H)-one (bentazone), 3,5-dibromo-4-hydroxy -benzonitrile (bromoxynil), 3,6-dichloro-2-methoxybenzoic acid (dicamba),2,4-dichloro -phenoxyacetic acid (2,4-D),O-(6-chloro-3-phenyl-pyridazin-4-yl)S-octyl thiocarbonate (pyridate),(4-amino-3, 5-dichloro-6-fluoro-pyridin-2-yl-oxy)-acetic acid (fluroxypyr), N -(2,6-difluoro-phenyl)-5-methyl-1,2,4-triazolo[1,5-a]-pyrimidine-2-sulphonamide -(flumetsulam, DE-498), N-(2,6-dichloro-3-methyl-phenyl)-5,7-dimethoxy-1,2,4-triazolo[1,5-a]-pyrimidine-2-sulphonamide (metosulam, DE-511), N-(4-methoxy-6-methyl-1,3,5-triazin-2-yl)-N'-(2-(3,3,3-trifluoropropyl)-phenylsulphonyl)-urea (prosulfuron), 5-N-(4-chloro-2-fluoro-5-methoxycarbonylmethylthio-phenyl)-imino) -tetrahydro-3-oxo-1H,3H-1,3,4-thiadiazolo,[3,4-a]-pyridazine(KIH-9201),2-(2-chloro -4-methylsulphonyl-benzoyl)cyclohexane-1,3-dione (sulcotrione), N'-(4-(3,4-dihydro-2-methoxy-2,4,4-trimethyl-2H-1-benzopyran-7-yloxy)-phenyl)-N-methoxy-N-methyl-urea (metobenzuron, UMP-488), 3-amino-2,5-dichloro-benzoic acid (chloramben), 2-(2-chloro-phenyl-methyl)-4,4-dimethyl-isoxazolidin-3-one (clomazone),2-(2,4-dichloro-5-methylsulphonylamino-phenyl)-4-difluoromethyl-5-methyl-2,4-dihydro-3H-1,2,4-triazol -3-one(sulfentrazone, F-6285),2-(4,5-dihydro-4-methyl-4-propyl-5-oxo-1H-imidazol-2-yl)-5-ethyl-pyridine-3-carboxylic acid (imazethapyr), 2-(4,5-dihydro-4-methyl-4-i -propyl-5-oxo-1H-imidazol-2-yl)-5-methyl-pyridine-3-carboxylic acid (imazamethapyr), 5-(2-chloro-trifluoromethyl-phenoxy)-2-nitro-benzoic acid ethoxycarbonylmethylester (fluoroglycofen-ethyl),4-dipropylamino-3,5-dinitro-benzenesulphonamide(oryzalin),S-phenymethyl N,N-dipropyl-thiocarbamate(prosulfocarb),3-chloro-4-chloromethyl-1-(3-trifluoromethyl-phenyl)-pyrrolidin-2-one (fluorochloridone), 2-chloro-6-nitro-3-phenoxy-benzenamine (aclonifen), N'-(4-bromo-phenyl)-N-methoxy-N-methylurea (metobromuron),9-hydroxy-9H-fluoren-9-carboxylic acid (flurenol),7-chloro-3-methyl -quinoline-8-carboxylic acid (quinmerac), 4-hydroxy-3,5-diiodo-benzonitrile (ioxynil), N-(3-(1 -ethyl-1-methyl-propyl)-isoxazol-5-yl)2,6-dimethoxy-benzamide(isoxaben),N'-(3-chloro-4-methoxy-phenyl)-N,N-dimethyl-urea(metoxuron), N-butyl-N'-(3,4-dichloro -phenyl)-N-methyl-urea (neburon), (4chloro-2-methyl-phenoxy)-acetic acid(MCPA) ,2-(4-chloro-2-methyl-phenoxy)-propionic acid (mecoprop), 3,5-dibromo-4-hydroxy-benzaldehyde O-(2,4-dinitro-phenyl) oxime (bromofenoxim), 4-chloro-2-oxo-3(2H)-benzopthiazoleacetic acid (benazolin), 3,6-dichloro-pyridine-2-carboxylic acid (clopyralid), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (F-8426), 1-(4-chloro-3 -(2,2,3,3,3-pentafluoro-propoxymethyl)-phenyl)-5-phenyl-1H- 1,2,4-triazole-3-carboxamide (flupoxam), 6-(6,7-dihydro-6,6-dimethyl-3H, 5H-pyrrolo[2,1-c]-,2,4-thiadiazol-3-ylideneamino)-7-fluoro-4-(2-propinyl)-2H-1,4-benzoxazin-3(4H)-one (thidiazimin), N-(4,6-dimethoxy-pyrimidin-2-yl)-N'-(2-cyclopropylcarbonyl-phenyl-sulphonyl)-urea (AC-322140), 4-chloro-3-(4-chloro-2-fluoro-5-ethoxycarbonyl -methoxy)-5-difluoromethoxy-1-methyl-pyrazole(ET-751),N-butoxymethyl-2-chloro-N -(2,6-diethyl-phenyl)-acetamide (butachlor), 2-chloro-N-2,6-diethyl-phenyl)-N-(2-propoxy-ethyl)-acetamide (pretilachlor), S-(phenylmethyl) N-ethyl-N-(1,2-dimethyl-propyl)-thiocarbamate (esprocarb), N-(4-methyl-phenyl)-N'-(1-methyl-1-phenyl-ethyl)-urea (dymron), 4-(2,4-dichloro-benzoyl)-1,3-dimethyl-5-(4-methyl-phenyl -sulphonyloxy)-pyrazole(pyrazolate), 4-(2,4-dichloro-benzoyl)-1,3-dimethyl-5-(phenyl- -carbonylmethoxy)-pyrazole (pyrazoxyfen), N-(4,6-dimethoxy-1,3,5-triazin-2-yl)-N'-(2-(2-methoxy-ethoxy)-phenylsulphonyl)-urea (cinosulfuron), N-(4,6-dimethoxy-pyrimidin -2-yl)-N'-(4-ethoxycarbonyl-1-methyl-pyrazol-5-yl-sulphonyl)-urea (pyrazosulfuron-ethyl), N-(4,6-dimethoxy-pyrimidin-2-yl)-N'-(2-chloro-imidazo[1,2-a]-pyridin-3-yl-sulphonyl)-urea (imazosulfuron), S,S-dimethyl 2-difluoromethyl-4-i-butyl-6-trifluoromethyl-pyridine-3,5-dicarbothioate (dithiopyr), 2-bromo-3,3-dimethyl-N-(1-methyl-1-phenyl-ethyl)-butanamide (bromobutide), 2-(2-naphthyloxy)-N-phenyl-propanamide (naproanilide),2-chloro-N-(2,6-dimethyl-phenyl)-N-(3-methoxy-2-thienyl-methyl)-acetamide (thenylchlor), 1,3,5-trichloro-2-(4-nitro-phenoxy)-benzene (chlornitrofen),2,4-dichloro-1-(3-methoxy-4-nitro-phenoxy)-benzene(chlomethoxyfen) ("active compounds of group 2") - and/or (c) a compound which improves the tolerance by crop plants, from the following group of compounds: a-(1,3-dioxolan-2-yl-methoximino)-phenylacetonitrile (oxabetrinil), a-(cyanomethoximino)-phenylacetonitrile (cyometrinil), 4-chloro-N-(1,3-dioxolan-2-yl-methoxy)-a-trifluoro-acetophenone oxime (fluxofenim), 4,6-dichloro-2-phenyl-pyrimidine (fenclorim), 4-dichloroacetyl-3,4-dihydro-3-methyl-2H-1,4-benzoxazine (benoxacor),5-chloro-quinoxalin-8-oxy-acetic acid 1-methyl-hexyl ester (cloquintocet), 2,2-dichloro-N-(2-oxo-2-(2-propenylamino)-ethyl)-N-(2-propenyl)- acetamide (DKA-24), 1,8-naphthalicanhydride,1-(2,4-dichloro-phenyl)-5-trichloromethyl-1H-1,2,4-triazole-3 -carboxylic acid ethyl ester (fenchlorazol-ethyl),2-chloro-4-trifluoromethyl-thiazole-5-carboxylic acid phenylmethyl ester (flurazole), 3-dichloroacetyl-5-(2-furanyl)-2,2-dimethyl-oxazolidine (furilazole,MON-13900),4-dichloroacetyl-1-oxa-4-azaspiro[4.5]-decane (AD-67),2-dichloromethyl-2-methyl-1,3-dioxolane (MG-191),2,2-dichloro-N -(1,3-dioxolan-2-yl-methyl-N-(2-propenyl)-acetamide(PPG-1292),2,2-dichloro-N, N-di-2-propenyl-acetamide(dichlormid),N-(4-methyl-phenyl)-N'-(1-methyl-1-phenyl-ethyl)-urea (dymron), 1-dichloroacetyl-hexahydro-3,3,8a-trimethylpyrrolo[1,2-a]-pyrimidin-6(2H)-one (BAS-145138), N-(2-methoxy-benzoyl)-4-(methylaminocarbonylamino) -benzenesulphonamide - ("antidotes" or "safeners") -in general, from 0.001 to 1000 parts by weight of an active compound of group 2 and/or from 0.001 to 1000 parts by weight of one of the above-mentioned antidotes/safeners being present per part by weight of an active compound of group 1 (i.e. of the formula (I)).

Selective-herbicidal compositions according to the invention which are of particular interest are characterized by a content of an active compound combination of (a) a heteroaryloxy-acetamide of the general formula (I) in which Het represents 1,2,4-thiadiazolyl or 1,3,4-thiadiazolyl, which is substituted by fluorine, chlorine, bromine or by methyl, ethyl, n- or i-propyl or phenyl, each of which is optionally substituted by fluorine and/or chlorine, and Ar represents phenyl which is optionally substituted by fluorine, chlorine, bromine, methyl or trifluoromethyl, ("active compounds of group 1") and (b) one or two compounds from a second group of herbicides which contains the active compounds mentioned below: N-(4,6-dimethoxy-pyrimidin-2-yl)-N'-(3-chloro-4-methoxycarbonyl-1-methyl-pyrazol-5 -yl-sulfonyl-urea (clopyrasulfuron,halosulfuron,NC-319),2-chloro-N-(2,4-dimethyl-3-thienyl)-N-(2-methoxy-1-methyl-ethyl)-acetamide(dimethenamid, SAN-582),2-chloro -N-(2,6-dimethyl-phenyl)-N-(1H-pyrazol-1-yl-methyl)-acetamide (metazachlor),N-(4,6-dimethoxy-pyrimidin-2-yl)-N'-(3-ethylsulfonyl-pyridin-2-yl-sulfonyl)-urea (rimsulfuron), 3-i-propyl-1H-2,1,3-benzothiadiazin-4(3H)-one (bentazone), 3,5-dibromo-4-hydroxy-benzonitrile (bromoxynil),3,6-dichloro-2-methoxybenzoic acid (dicamba),2,4-dichloro-phenoxyacetic acid (2,4-D),O-(6-chloro-3-phenyl-pyridazin-4-yl)S-octyl thiocarbonate (pyridate),(4-amino-3,5-dichloro-6-fluoro-pyridin-2-yl-oxy)-acetic acid (fluroxypyr), N-(2,6-difluoro-phenyl)-5-methyl-1,2,4-triazolo[1,5-a]-pyrimidine-2-sulphonamide (flumetsulam, DE-498), N-(2,6-dichloro-3-methyl-phenyl)-5,7-dimethoxy-1,2,4-triazolo [1,5-a]-pyrimidine-2-sulphonamide (metosulam, DE-511), N-(4-methoxy-6-methyl-1,3,5-triazin-2-yl)-N'-(2-(3,3,3-trifluoropropyl)-phenylsulphonyl)-urea (prosulfuron), 5-(N-(4-chloro-2-fluoro-5-methoxycarbonylmethylthio-phenyl)-imino)-tetrahydro-3-oxo-1H,3H-1,3,4-thiadiazolo[3,4-a]-pyridazine(KIH-9201),2-(2-chloro-4-methylsulphonyl-benzoyl)cyclohexane-1,3-dione (sulcotrione), N'-(4-(3,4-dihydro-2-methoxy-2,4,4-trimethyl-2H-1-benzopyran-7-yl-oxy)-phenyl)-N-methoxy-N-methyl-urea (metobenzuron, UMP-488), 3-amino-2,5-dichloro-benzoic acid (chloramben), 2-(2-chloro-phenyl-methyl)-4,4-dimethyl-isoxazolidin-3-one (clomazone),2-(2,4-dichloro-5-methylsulphonylamino-phenyl)-4-difluoromethyl-5-methyl-2,4-dihydro-3H-1,2,4-triazol-3-one (sulfentrazone, F-6285),2-(4,5-dihydro-4-methyl-4-i-propyl-5-oxo-1H-imidazol-2-yl)-5-ethyl-pyridine-3-carboxylic acid (imazethapyr), 2-(4,5-dihydro-4-methyl-4-i-propyl-5-oxo-1H-imidazol-2-yl)-5-methyl-pyridine-3-carboxylic acid (imazamethapyr), 5-(2-chloro-4-trifluoromethyl-phenoxy)-2-nitro-benzoic acidethoxycarbonylmethylester (fluoroglycofen-ethyl),4-diproplamino-3,5-dinitro-benzenesulphonanmide(oryzalin),S-phenylmethyl N,N-dipropyl-thiocarbamate (prosulfocarb),3-chloro-4-chloromethyl-1-(3-trifluoromethyl-phenyl)-pyrrolidin-2-one (fluorochloridone),2-chloro-6-nitro-3-phenoxy-benzenamine (aclonifen), N'-(4-bromo-phenyl)-N-methoxy-N-methylurea (metobromuron),9-hydroxy-9H-fluoren-9-carboxylic acid(flurenol),7-chloro-3-methyl -quinoline-8-carboxylic acid (quinmerac),4-hydroxy-3,5-diiodo-benzonitrile (ioxynil), N-(3-(1-ethyl-1-methyl-propyl)-isoxazol-5-yl)-2,6-dimethoxy-benzamide(isoxaben), N'-(3-chloro-4-methoxy-phenyl)-N,N-dimethyl-urea(metoxuron), N-butyl-N'-(3,4-dichloro -phenyl)-N-methyl-urea(neburon), (4-chloro-2-methyl-phenoxy)-acetic acid (MCPA), 2-(4-chloro-2-methyl-phenoxy)-propionic acid (mecoprop), 3,5-dibromo-4-hydroxy-benzaldehyde O-(2,4-dinitro-phenyl) oxime (bromofenoxim), 4-chloro-2-oxo-3(2H)-benzothiazoleacetic acid (benazolin), 3,6-dichloro-pyridine-2carboxylic acid (clopyralid), 2-(4-chloro-2-fluoro-5-(2-chloro-2-ethoxycarbonyl-ethyl)-phenyl) -4-difluoromethyl-5-methyl-2,4-dihydro-3H-1,2,4-triazol-3-one (F-8426), 1-(4-chloro-3-(2,2,3,3,3-pentafluoro-propoxymethyl)-phenyl)-5-phenyl-1H-1,2,4-triazole-3-carboxamide (flupoxam), 6-(6,7-dihydro-6,6-dimethyl-3H,5H-pyrrolo[2,1-c]-1,2,4-thiadiazol-3-ylideneamino)-7-fluoro-4-(2-propinyl)-2H-1,4-benzoxazin-3(4H)-one (thidiazimin), N-(4,6-dimethoxy-pyrimidin-2-yl)-N'-(2-cyclopropylcarbonyl-phenyl-sulphonyl)-urea (AC-322140), 4-chloro-3-(4-chloro-2-fluoro-5-ethoxycarbonyl -methoxy)-5-difluoromethoxy-1-methyl-pyrazole(ET-751),N-butoxymethyl-2-chloro-N -(2,6-diethyl-phenyl)-acetamide (butachlor), 2-chloro-N-2,6-diethyl-phenyl)-N-(2-propoxy-ethyl)-acetamide (pretilachlor), S-(phenylmethyl) N-ethyl-N-(1,2-dimethyl -propyl)-thiocarbamate (esprocarb), N-(4- methyl-phenyl)-N'-(1-methyl-1-phenyl-ethyl)-urea (dymron), 4-(2,4-dichloro-benzoyl)-1,3-dimethyl-5-(4-methyl-phenyl -sulphonyloxy)-pyrazole (pyrazolate), 4-(2,4-dichloro-benzoyl)-1,3-dimethyl-5-(phenyl-carbonylmethoxy)-pyrazole (pyrazoxyfen), N-(4,6-dimethoxy-1,3,5-triazin-2-yl)-N'-(2-(2-methoxy-ethoxy)-phenylsulphonyl)-urea (cinosulfuron), N-(4,6-dimethoxy-pyrimidin -2-yl)-N'-(4-ethoxycarbonyl-1-methyl-pyrazol-5-yl-sulphonyl)-urea (pyrazosulfuron-ethyl, N-(4,6-dimethoxy-pyrimidin-2-yl)-N'-(2-chloro-imidazo[1,2-$a$]-pyridin-3-yl-sulphonyl)-urea (imazosulfuron), S,S-dimethyl 2-difluoromethyl-4i-i-butyl-6-trifluoromethyl-pyridine-3,5-dicarbothioate (dithiopyr), 2-bromo-3,3-dimethyl-N-(1-methyl-1-phenyl-ethyl)-butanamide (bromobutide), 2-(2-naphthyloxy)-N-phenyl-propanamide (naproanilide),2-chloro-N-(2,6-dimethyl-phenyl)-N-(3-methoxy-2-thienyl -methyl)-acetamide (thenylchlor), 1,3,5-trichloro-2-(4-nitro-phenoxy)-benzene (chlornitrofen),2,4-dichloro-1-(3-methoxy-4-nitro-phenoxy)-benzene (chlomethoxyfen)

-("active compounds of group 2") - and/or (c) a compound which improves the tolerance by crop plants, from the following group of compounds: $a$-(1,3-dioxolan-2-yl-methoximino)-phenylacetonitrile (oxabetrinil), $a$-(cyanomethoximino)-phenylacetonitrile (cyometrinil), 4-chloro-N-(1,3-dioxolan-2-yl -methoxy)-$a$-trifluoro-acetophenone oxime (fluxofenim), 4,6-dichloro-2-phenyl- pyrimidine (fenclorim), 4-dichloroacetyl-3,4-dihydro-3-methyl-2H-1,4-benzoxazine (benoxacor),5-chloro-quinoxalin-8-oxy-acetic acid 1-methyl-hexyl ester (cloquintocet), 2,2-dichloro-N-(2-oxo-2-(2-propenylamino)-ethyl)-N-(2-propenyl)-acetamide (DKA-24), 1,8-naphthalicanhydride,1-(2,4-dichloro-phenyl)-5-trichloromethyl-1H-1,2,4-triazole-3-carboxylic acid ethyl ester (fenchlorazol-ethyl),2-chloro-4-trifluoromethyl-thiazole-5-carboxylic acid phenylmethyl ester (flurazole), 3-dichloroacetyl-5-(2-furanyl)-2,2-dimethyl-oxazolidine (furilazole,MON-13900),4-dichloroacetyl-1-oxa-4-azaspiro[4.5]-decane (AD-67),2-dichloromethyl-2-methyl-1,3-dioxolane(MG-191),2,2-dichloro-N -(1,3-dioxolan-2-yl-methyl)-N-(2-propenyl)-acetamide(PPG-1292),2,2-dichloro-N,N-di-2-propenyl-acetamide(dichlormid), N-(4-methyl-phenyl)-N'-(1-methyl-1-phenyl-ethyl)-urea (dymron), 1-dichloroacetyl-hexahydro-3,3,8$a$-trimethylpyrrolo[1,2-$a$]-pyrimidin-6(2H-one (BAS-145138), N-(2-methoxy-benzoyl)-4-(methylaminocarbonylamino) -benzenesulphonamide - ("antidotes" or "safeners") -in general, from 0.01 to 100 parts by weight of an active compound of group 2 and/or from 0.01 to 100 parts by weight of one of the abovementioned antidotes/safeners being present per part by weight of an active compound of group 1 (i.e. of the formula (I)).

Selective-herbicidal compositions according to the invention which are of very special interest are characterized by a content of an active compound combination consisting of (a) a heteroaryloxy-acetamide of the formula (I) in which Het represents 1,2,4-thiadiazolyl or 1,3,4thiadiazolyl, which is substituted by chlorine, dichloromethyl, difluoromethyl, trichloromethyl, trifluoromethyl, chlorodifluoromethyl, fluorodichloromethyl or pentafluoroethyl, and Ar represents phenyl which is optionally substituted by fluorine, chlorine, methyl or trifluoromethyl, ("active compounds of group 1") and (b) one or two compounds from a second group of herbicides which contains the active compounds mentioned below: N-(4,6-dimethoxy-pyrimidin-2-yl)-N'-(3-chloro-4-methoxycarbonyl-1-methyl-pyrazol-5-yl-sulfonyl)-urea (clopyrasulfuron, halosulfuron, NC-319), 2-chloro-N-2,4-dimethyl-3-thienyl)-N-(2-methoxy-1-methyl-ethyl)-acetamide(dimethenamid, SAN-582),2-chloro -N-(2,6-dimethyl-phenyl)-N-(1H-pyrazol-1-yl-methyl)-acetamide (metazachlor), N-(4,6-dimethoxy-pyrimidin-2-yl)-N'-(3-ethylsulfonyl-pyridin-2-yl-sulfonyl)-urea (rimsulfuron), 3-i-propyl-1H-2,1,3-benzothiadiazin-4(3H)-one (bentazone), 3,5-dibromo-4-hydroxy-benzonitrile (bromoxynil),3,6-dichloro-2-methoxybenzoic acid(dicamba),2,4-dichloro-phenoxyacetic acid(2,4-D),O-(6-chloro-3-phenyl-pyridazin-4-yl)S-octyl thiocarbonate (pyridate),(4-amino-3,5-dichloro-6-fluoro-pyridin-2-yl-oxy)-acetic acid (fluroxypyr), N-(2,6-difluoro-phenyl)-5-methyl-1,2,4-triazolo[1,5-$a$]-pyrimidine-2-sulphonamide (flumetsulam, DE-498), N-(2,6-dichloro-3-methyl-phenyl)-5,7-dimethoxy-1,2,4-triazolo [1,5-$a$]-pyrimidine-2-sulphonamnide (metosulam, DE-511), N-(4-methoxy-6-methyl-1,3,5-triazin-2-yl)-N'-(2-(3,3,3-trifluoropropyl)-phenylsulphonyl)-urea (prosulfuron), 5-(N-(4-chloro-2-fluoro-5-methoxycarbonylmethylthio-phenyl)-imino) -tetrahydro-3-oxo-1H,3H-1,3,4-thiadiazolo[3,4-$a$]-pyridazine(KIH-9201),2-(2-chloro-4-methylsulphonyl-benzoyl)cyclohexane-1,3-dione (sulcotrione), N'-(4-(3,4-dihydro-2-methoxy-2,4,4-trimethyl-2H-1-benzopyran-7-yl-oxy)-phenyl)-N-methoxy-N-methyl-urea (metobenzuron, UMP-488), 3-amino-2,5-dichloro-benzoic acid (chloramben), 2-(2-chloro-phenyl-methyl)-4,4-dimethyl-isoxazolidin-3-one(clomazone),2-(2,4-dichloro-5-methylsulphonylamino-phenyl)-4-difluoromethyl-5-methyl-2,4-dihydro-3H-1,2,4-triazol -3-one (sulfentrazone, F-6285),2-(4,5-dihydro-4-methyl-4-i-propyl-5-oxo-1H-imidazol-2-yl)-5-ethyl-pyridine-3-carboxylic acid (imazethapyr), 2-(4,5-dihydro-4-methyl-4-i-propyl-5-oxo-1H-imidazol-2-yl)-5-methyl-pyridine-3-carboxylic acid (imazamethapyr), 5-(2-chloro-4-trifluoromethyl-phenoxy)-2-nitro-benzoicacidethoxycarbonylmethylester (fluoroglycofen-ethyl),4-dipropylamino-3,5-dinitro-benzenesulphonamide(oryzalin),S-phenylmethyl N,N-dipropyl-thiocarbamate(prosulfocarb), 3-chloro-4-chloromethyl-1-(3-trifluoromethyl-phenyl)-pyrrolidin-2-one (fluorochloridone), 2-chloro-6-nitro-3-phenoxy-benzenamine (aclonifen), N'-(4-bromo-phenyl)-N-methoxy-N-methylurea(metobromuron), 9-hydroxy-9H-fluoren-9-carboxylic acid(flurenol),7-chloro-3-methyl-quinoline-8-carboxylic acid (quinmerac) (quinmerac), 4-hydroxy-3,5-diiodo-benzonitrile (ioxynil), N-(3-(1-ethyl-1-methyl-propyl)-isoxazol-5-yl)-2,6-dimethoxy-benzamide (isoxaben), N'-(3-chloro-4-methoxy-phenyl)-N,N-dimethyl-urea(metoxuron),N-butyl-N'-(3,4-dichloro -phenyl)-N-methyl-urea(neburon),(4-chloro-2-methyl-phenoxy)-acetic acid (MCPA), 2-(4-chloro-2-methyl-phenoxy)-propionic acid (mecoprop), 3,5-dibromo-4-hydroxy -benzaldehyde O-(2,4-dinitro-phenyl) oxime (bromofenoxim), 4-chloro-2-oxo-3(2H)-benzothiazoleacetic acid (benazolin), 3,6-dichloro-pyridine-2-carboxylic acid (clopyralid), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (F-8426), 1-(4-chloro-3-(2,2,3,3,3-pentafluoro-propoxymethyl)-phenyl)-5-phenyl-1H-1,2,4-triazole-3-carboxamide (flupoxam), 6-(6,7-dihydro-6,6-dimethyl-3H,5H-pyrrolo[2,1-$c$]-1,2,4 -thiadiazol-3-ylideneamino)-7-fluoro-4-(2-propinyl)-2H-1,4-benzoxazin-3(4H)-one (thidiazimin), N-(4,6-dimethoxy-pyrimidin-2-yl)-N'-(2-cyclopropylcarbonyl-phenyl-sulphonyl)-urea (AC-322140), 4-chloro-3-(4-chloro-2-fluoro-5-ethoxycarbonyl-methoxy)5-difluoromethoxy-1-methyl-pyrazole(ET-751), N-butoxymethyl-2-chloro-N -(2,6-diethyl-phenyl)- acetamide (butachlor), 2-chloro-N-(2,6-diethyl-phenyl)-N-(2-propoxy-ethyl-acetamide (pretilachlor), S-(phenylmethyl) N-ethyl-N-(1,2-dimethyl -propyl)-thiocarbamate (esprocarb), N-(4-methyl-phenyl)-N'-(1-methyl-1-phenyl-ethyl)-urea (dymron), 4-(2,4-dichloro-benzoyl)-1,3-dimethyl-5-(4-methyl-phenyl -sulphonyloxy-pyrazole (pyrazolate), 4-(2,4-dichloro-benzoyl)-1,3-dimethyl-5-(phenyl -carbonylmethoxy)-pyrazole (pyrazoxyfen), N-(4,6-dimethoxy-1,3,5-triazin-2-yl)-N'-(2-(2-methoxy-ethoxy)-phenylsulphonyl)-urea (cinosulfuron), N-(4,6-dimethoxy-pyrimidin -2-yl)-N'-(4-ethoxycarbonyl-1-methyl-pyrazol-5-yl-sulphonyl)-urea (pyrazosulfuron-ethyl), N-(4,6-dimethoxy-pyrimidin-2-yl)-N'-(2-chloro-imidazo[1,2-a]-pyridin-3-yl-sulphonyl)-urea (imazosulfuron), S,S-dimethyl 2-difluoromethyl-4-i-butyl-6-trifluoromethyl-pyridine-3,5-dicarbothioate (dithiopyr), 2-bromo-3,3-dimethyl-N-(1-methyl-1-phenyl-ethyl)-butanamide (bromobutide), 2-(2-naphthyloxy)-N-phenyl-propanamide (naproanilide),2-chloro-N-(2,6-dimethyl-phenyl)-N-(3-methoxy-2-thienyl -methyl)-acetamide (thenylchlor), 1,3,5-trichloro-2-(4-nitro-phenoxy)-benzene (chlornitrofen),2,4-dichloro-1-(3-methoxy-4-nitro-phenoxy)-benzene (chlomethoxyfen) -("active compounds of group 2") - and/or (c) a compound which improves the tolerance by crop plants, from the following group of compounds: a-(1,3-dioxolan-2-yl-methoximino)-phenylacetonitrile (oxabetrinil), a-(cyanomethoximino)-phenylacetonitrile (cyometrinil), 4-chloro-N-(1,3-dioxolan-2-yl -methoxy)-a-trifluoro-acetophenone oxime (fluxofenim), 4,6-dichloro-2-phenyl-pyrimidine (fenclorim), 4-dichloroacetyl-3,4-dihydro-3-methyl-2H-1,4-benzoxazine (benoxacor), 5-chloro-quinoxalin-8-oxy-acetic acid 1-methyl-hexyl ester (cloquintocet), 2,2-dichloro-N-(2-oxo-2-(2-propenylamino) -ethyl)-N-(2-propenyl)-acetamide (DKA-24), 1,8-naphthalicanhydride,1-(2,4-dichloro-phenyl)-5-trichloromethyl-1H-1,2,4-triazole-3-carboxylic acid ethyl ester (fenchlorazol-ethyl), 2-chloro-4-trifluoromethyl-thiazole-5-carboxylic acid phenylmethyl ester (flurazole), 3-dichloroacetyl-5-(2-furanyl)-2,2-dimethyl-oxazolidine (furilazole,MON-13900),4-dichloroacetyl-1-oxa-4-azaspiro[4.5]-decane(AD-67), 2-dichloromethyl-2-methyl-1,3-dioxolane(MG-191), 2,2-dichloro-N -(1,3-dioxolan-2-yl-methyl)-N-(2-propenyl)-acetamide(PPG-1292),2,2-dichloro-N, N-di-2-propenyl-acetamide(dichlormid),N-(4-methyl-phenyl)-N'-(1-methyl-1-phenyl-ethyl)-urea (dymron), 1-dichloroacetyl-hexahydro-3,3,8a-trimethylpyrrolo[1,2-a]-pyrimidin-6(2H)-one (BAS-145138), N-(2-methoxy-benzoyl)-4-(methylaminocarbonylamino) -benzenesulphonamide - ("antidotes" or "safeners") -in general, from 0.1 to 10 parts by weight of an active compound of group 2 and/or from 0.1 to 10 parts by weight of one of the abovementioned antidotes/safeners being present per part by weight of an active compound of group 1 (i.e. of the formula (I)).

A particularly preferred group of selective-herbicidal compositions according to the invention is characterized by a content of an active compound combination consisting of (a) a heteroaryloxy-acetamide of the formula (I) in which
Het represents 1,2,4-thiadiazolyl or 1,3,4-thiadiazolyl, which is substituted by chlorine, dichloromethyl, difluoromethyl, trichloromethyl, trifluoromethyl, chlorodifluoromethyl, fluorodichloromethyl or pentafluoroethyl, and Ar represents phenyl which is optionally substituted by fluorine, chlorine, methyl or trifluoromethyl,
("active compounds of group 1") and (b) one compound from a second group of herbicides which contains the active compounds mentioned below: N-(4,6-dimethoxy-pyrimidin-2-yl)-N'-(3-chloro-4-methoxycarbonyl-1-methyl-pyrazol-5-yl-sulfonyl)-urea (clopyrasulfuron, halosulfuron,NC-319),2-chloro-N-(2,4-dimethyl-3-thienyl)-N-(2-methoxy-1-methyl-ethyl)-acetamide(dimethenamid, SAN-582), 2-chloro -N-(2,6-dimethyl-phenyl)-N-(1H-pyrazol-1-yl-methyl)-acetamide (metazachlor),N-(4,6-dimethoxy-pyrimidin-2-yl)-N'-(3-ethylsulfonyl-pyridin-2-yl-sulfonyl)-urea (rimsulfuron), 3-i-propyl-1H-2,1,3-benzothiadiazin-4(3H)-one (bentazone), 3,5-dibromo-4-hydroxy-benzonitrile (bromoxynil). 3,6-dichloro-2-methoxybenzoic acid (dicamba),2,4-dichloro-phenoxyacetic acid(2,4-D),O-(6-chloro-3-phenyl-pyridazin-4-yl)S-octyl thiocarbonate (pyridate),(4-amino-3,5-dichloro-6-fluoro-pyridin-2-yl-oxy)-acetic acid(fluroxypyr), N-(2,6-difluoro-phenyl)-5-methyl-1,2,4-triazolo[1,5-a]-pyrimidine-2-sulphonamide (flumetsulam, DE-498), N-(2,6-dichloro-3-methyl-phenyl)-5,7-dimethoxy-1,2,4-triazolo [1,5-a]-pyrimidine-2-sulphonamide (metosulam, DE-511), N-(4-methoxy-6 -methyl-1,3,5-triazin-2-yl)-N'-(2-(3,3,3-trifluoropropyl)-phenylsulphonyl)-urea (prosulfuron), 5-(N-(4-chloro-2-fluoro-5-methoxycarbonylmethylthio-phenyl)-imino) -tetrahydro-3-oxo-1H-1,3,4-thiadiazolo[3,4-a]-pyridazine (KIH-9201),2-(2-chloro-4-methylsulphonyl-benzoyl)cyclohexane-1,3-dione (sulcotrione), N'-(4-(3,4-dihydro-2-methoxy-2,4,4-trimethyl-2H-1-benzopyran-7-yl-oxy-phenyl)-N-methoxy-N-methyl-urea (metobenzuron, UMP-488), 3-amino-2,5-dichloro-benzoic acid (chloramben), 2-(2-chloro-phenyl-methyl)-4,4-dimethyl-isoxazolidin-3-one(clomazone),2-(2,4-dichloro-5-methylsulphonylamino-phenyl)-4-difluoromethyl-5-methyl-2,4-dihydro-3H-1,2,4-triazol-3-one (sulfentrazone, F-6285),2-(4,5-dihydro-4-methyl-4-i-propyl-5-oxo-1H-imidazol-2-yl)-5-ethyl-pyridine-3-carboxylic acid (imazethapyr), 2-(4,5-dihydro-4-methyl-4-i-propyl-5-oxo-1H-imidazol-2-yl)-5-methyl-pyridine-3-carboxylic acid (imazamethapyr), 5-(2-chloro-4-trifluoromethyl-phenoxy)-2-nitro-benzoicacidethoxycarbonylmethylester (fluoroglycofen-ethyl),4-dipropylamino-3,5-dinitro-benzenesulphonamide(oryzalin), S-phenylmethyl N,N-dipropyl-thiocarbamate(prosulfocarb),3-chloro-4-chloromethyl-1-(3-trifluoromethyl-phenyl)-pyrrolidin-2-one (fluorochloridone),2-chloro-6-nitro-3-phenoxy-benzenamine (aclonifen), N'-(4-bromo-phenyl)-N-methoxy-N-methylurea (metobromuron),9-hydroxy-9H-fluoren-9-carboxylic acid(flurenol),7-chloro-3-methyl -quinoline-8-carboxylic acid (quinmerac), 4-hydroxy-3,5-diiodo-benzonitrile (ioxynil), N-(3-(1-ethyl-1-methyl-propyl)-isoxazol-5-yl)-2,6-dimethoxy-benzamide(isoxaben),N'-(3-chloro-4-methoxy-phenyl)-N,N-dimethyl-urea(metoxuron), N-butyl-N'-(3,4-dichloro -phenyl)-N-methyl-urea(neburon), (4-chloro-2-methyl-phenoxy)-acetic acid (MCPA),2-(4-chloro-2-methyl-phenoxy)-propionic acid (mecoprop), 3,5-dibromo-4-hydroxy -benzaldehyde O-(2,4-dinitro-phenyl) oxime (bromofenoxim), 4-chloro-2-oxo-3(2H)-benzothiazoleacetic acid (benazolin), 3,6-dichloro-pyridine-2-carboxylic acid (clopyralid), 2-(4-chloro-2-fluoro-5-(2-chloro-2-ethoxycarbonyl-ethyl)-phenyl) -4-difluoromethyl-5-methyl-2,4-dihydro-3H-1,2,4-triazol-3-one (F-8426), 1-(4-chloro-3-(2,2,3,3,3-pentafluoro-propoxymethyl)-phenyl)-5-phenyl-1H-1,2,4-triazole-3-carboxamide (flupoxam), 6-(6,7-dihydro-6,6-dimethyl-3H-5H-pyrrolo[2,1-c]-1,2,4-thiadiazol-3-ylideneamino)-7-fluoro-4-(2-propinyl)-2H-1,4-benzoxazin-3(4H)-one (thidiazimin), N-(4,6-dimethoxy-pyrimidin-2-yl)-N'-(2-cyclopropylcarbonyl-phenyl-sulphonyl)-urea (AC-322140), 4-chloro-3-(4-chloro-2-fluoro-5-ethoxycarbonyl -methoxy)-5-difluoromethoxy-1-methyl-pyrazole(ET-751),N-butoxymethyl-2-chloro-N -(2,6-diethyl-phenyl)-acetamide (butachlor), 2-chloro-N-(2,6-diethyl-phenyl)-N-(2-propoxy-ethyl)-acetamide (pretilachlor), S-phenylmethyl) N-ethyl-N-(1,2-dimethyl -propyl)-thiocarbamate (esprocarb), N-(4-methyl-phenyl)-N'-(1-methyl-1-phenyl-ethyl)-urea (dymron), 4-(2,4-dichloro-benzoyl)-1,3-dimethyl-5-(4-methyl-phenyl -sulphonyloxy)-pyrazole (pyrazolate), 4-(2,4-dichloro-benzoyl)-1,3-dimethyl-5-(phenyl-carbonylmethoxy-pyrazole (pyrazoxyfen),N-(4,6-dimethoxy-1,3,5-triazin-2-yl)-N'-(2-(2-methoxy-ethoxy)-phenylsulphonyl)-urea (cinosulfuron), N-(4,6-dimethoxy-pyrimidin -2-yl)-N'-(4-ethoxycarbonyl-1-methyl-pyrazol-5-yl-sulphonyl)-urea (pyrazosulfuron-ethyl), N-(4,6-dimethoxy-pyrimidin-2-yl)-N'-(2-chloro-imidazo[1,2-a]-pyridin-3-yl-sulphonyl)-urea (imazosulfuron), S,S-dimethyl 2-difluoromethyl-4-i-butyl-6-trifluoromethyl-pyridine-3,5-dicarbothioate (dithiopyr), 2-bromo-3,3-dimethyl-N-(1-methyl-1-phenyl-ethyl)-butanamide (bromobutide), 2-(2-naphthyloxy)-N-phenyl-propanamide (naproanilide),2-chloro-N-(2,6-dimethyl-phenyl)-N-(3-methoxy-2-thienyl-methyl)-acetamide (thenylchlor), 1,3,5-trichloro-2-(4-nitro-phenoxy)-benzene (chlornitrofen), 2,4-dichloro-1-(3-methoxy-4-nitro-phenoxy)-benzene(chlomethoxyfen) -("active compounds of group 2").

A further particularly preferred group of selective-herbicidal compositions according to the invention is characterized by a content of an active compound combination consisting of (a) a heteroaryloxy-acetamide of the formula (I) in which Het represents 1,2,4-thiadiazolyl or 1,3,4-thiadiazolyl, which is substituted by chlorine, dichloromethyl, difluoromethyl, trichloromethyl, trifluoromethyl, chlorodifluoromethyl, fluorodichloromethyl or pentafluoroethyl, and Ar represents phenyl which is optionally substituted by fluorine, chlorine, methyl or trifluoromethyl, ("active compounds of group 1") and (b) a compound which improves the tolerance by crop plants, from the following group of compounds: a-(1,3-dioxolan-2-yl-methoximino)-phenylacetonitrile (oxabetrinil), a(cyanomethoximino)-phenylacetonitrile (cyometrinil), 4-chloro-N-(1,3-dioxolan-2-yl-methoxy)-a-trifluoro-acetophenone oxime (fluxofenim), 4,6-dichloro-2-phenyl-pyrimidine (fenclorim), 4dichloroacetyl-3,4-dihydro-3-methyl-2H-1,4-benzoxazine (benoxacor), 5-chloro-quinoxalin-8-oxy-acetic acid 1-methyl-hexyl ester (cloquintocet), 2,2-dichloro -N-(2-oxo-2-(2-propenylamino)-ethyl)-N-(2-propenyl)-acetamide (DKA-24), 1,8-naphthalic anhydride, 1-(2,4-dichloro-phenyl)-5-trichloromethyl-1H-1,2,4-triazole-3-carboxylic acid ethyl ester (fenchlorazol-ethyl),2-chloro-4-trifluoromethyl-thiazole-5- carboxylic acid phenylmethyl ester (flurazole), 3-dichloroacetyl-5-(2-furanyl)-2, 2-dimethyl-oxazolidine (furilazole,MON-13900),4-dichloroacetyl-1-oxa-4-azaspiro [4.5]-decane (AD-67), 2-dichloromethyl-2-methyl-1,3-dioxolane (MG-191),2,2-dichloro -N-(1,3-dioxolan-2-yl-methyl)-N-(2-propenyl)-acetamide(PPG-1292),2,2-dichloro-N,N -di-2-propenyl-acetamide (dichlormid), N-(4-methyl-phenyl)-N'-(1-methyl-1-phenyl-ethyl)-urea (dymron), 1-dichloroacetyl-hexahydro-3,3,8a-trimethylpyrrolo[1,2-a]-pyrimidin-6(2H)-one (BAS-145138), N-(2-methoxy-benzoyl)-4-(methylaminocarbonylamino) -benzenesulphonamide - ("antidotes" or "safeners").

Examples of the compounds of the formula (I) to be used as co-components according to the invention are: N-i-propyl-N-phenyl-a-(5-trifluoromethyl-1,3,4-thiadiazol-2-yl-oxy)-acetamide, N-i-propyl-N-(2-chloro-phenyl)-a-(5-trifluoromethyl-1,3,4-thiadiazol-2-yl-oxy)-acetamide, N-i-propyl-N-(3-chloro-phenyl)-a-(5-trifluoromethyl-1,3,4-thiadiazol-2-yl-oxy)-acetamide, N-i-propyl-N-(4-chloro-phenyl)-a-(5-trifluoromethyl-1,3,4-thiadiazol-2-yl-oxy)-acetamide, N-i-propyl-N-(2-fluoro-phenyl)-a-(5-trifluoromethyl-1,3,4-thiadiazol-2-yl-oxy)-acetamide, N-i-propyl-N-(3-fluoro-phenyl)-a-(5-trifluoromethyl-1,3,4-thiadiazol-2-yl-oxy)-acetamide, N-i-propyl-N-(4-fluoro-phenyl)-a-(5-trifluoromethyl -1,3,4-thiadiazol-2-yl-oxy)-acetamide, N-i-propyl-N-(2,4-difluoro-phenyl)-a-(5-trifluoromethyl-1,3,4-thiadiazol-2-yl-oxy)-acetamide, N-i-propyl-N-(3,4-difluoro -phenyl-a-(5-trifluoromethyl-1,3,4-thiadiazol-2-yl-oxy)-acetamide, N-i-propyl-N-(2-methyl-phenyl)-a-(5-trifluoromethyl-1,3,4-thiadiazol-2-yl-oxy-acetamide, N-i-propyl-N -(3-methyl-phenyl)-a-(5-trifluoromethyl-1,3,4-thiadiazol-2-yl-oxy)-acetamide, N-i-propyl-N-(4-methyl-phenyl)-a-(5-trifluoromethyl-1,3,4-thiadiazol-2-yl-oxy)-acetamide, N-i-propyl-N-(3-trifluoromethyl-phenyl)-a-(5-trifluoromethyl-1,3,4-thiadiazol-2-yl-oxy)-acetamide and N-i-propyl-N-(4-trifluoromethyl-phenyl)-a-(5-trifluoromethyl-1,3,4-thiadiazol-2-yl-oxy)-acetamide.

The compound N-i-propyl-N-(4-fluoro-phenyl)-a-(5-trifluoromethyl-1,3,4-thiadiazol-2-yl-oxy)-acetamide - referred to in the Use Examples as compound (I—1) - may be emphasized in particular as a co-component of the formula (I).

The compounds of the formula (I) are described in the abovementioned patent applications and patent documents.

Co-components from the active compounds of group 2 which may be emphasized in particular are: clopyrasulfuron (halosulfuron, NC-319), dimethenamid (SAN-582), metazachlor, rimsulfuron, bentazone, bromoxynil, dicamba, 2,4-D, pyridate, fluroxypyr, flumetsulam (DE-498), metosulam (DE-511), prosulfuron (CGA-152005), KIH-9201, sulcotrione, metobenzuron (UMP-488) and clopyralid.

It has now surprisingly been found that the above-defined active compound combinations of the heteroaryloxy-acetamides of the formula (I) and the above-listed active compounds of group 2 and/or the compounds which improve the tolerance by crop plants, from the above-listed group of antidotes/safeners, while exhibiting very good tolerance by crop plants, have a particularly high herbicidal activity and can be used in a variety of crops, especially in maize but also in soybean, potatoes, wheat, barley and rice, for the selective combating of weeds.

Surprisingly, the herbicidal activity of the active compound combinations according to the invention, comprising compounds of the above-listed groups 1 and 2, is considerably higher than the sum of the actions of the individual active compounds.

There is therefore an unforeseeable synergistic effect, and not just a supplementary action. The novel active compound combinations are well tolerated by numerous crops, with the novel active compound combinations also allowing good combating of weeds which are otherwise difficult to combat. The novel active compound combinations therefore represent a valuable enrichment of selective herbicides.

The compounds to be used in accordance with the invention as antidotes/safeners are particularly suitable for improving the tolerance by crop plants of active compounds of the formula (I), but also of active compounds of group 2, especially with respect to maize.

The active compound combinations according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Immium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cuburbita and Helianthus.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeumn, Avena, Secale, Sorghum, Panicum, Saccharum, Ananas, Asparagus and Allium. However, the use of the active compound combinations according to the invention is in no way restricted to these genera, but also extends in the same manner to other plants.

The synergistic effect of the active compound combinations according to the invention is particularly highly pronounced at certain concentration ratios. However, the weight ratios of the active compounds in the active compound combinations can be varied within relatively broad ranges. In general, per part by weight of active compound of the formula (I), there are from 0.001 to 1000 parts by weight, preferably from 0.01 to 100 parts by weight and particularly preferably from 0.1 to 10 parts by weight of active compound of group 2 and/or from 0.001 to 1000 parts by weight, preferably from 0.01 to 100 parts by weight and particularly preferably from 0.1 to 10 parts by weight of one of the compounds mentioned above under (c) which improves the tolerance by crop plants (antidotes/safeners).

The active compounds or active compound combinations can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example allylaryl polyglycol ethers, alkylsulphonates, alkylsulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compounds and, if desired, safener(s), preferably between 0.5 and 90%.

The active compound combinations according to the invention are employed in general in the form of finished formulations. The active compounds present in the active compound combinations, however, can also be mixed for use in individual formulations, i.e. applied in the form of tank mixes.

Furthermore, the novel active compound combinations, as such or in their formulations, can also be used as mixtures with other known herbicides, in which case finished formulations or tank mixes are in turn possible. Mixtures with other known active compounds, such as fungicides, insecticides, acaricides, nematicides, bird repellants, growth substances, plant nutrients and agents which improve soil structures, are also possible. For specific applications, especially post-emergence application, it may also be advantageous to incorporate into the formulations, as further additives, plant- compatible mineral or vegetable oils (e.g. the commercial preparation "Oleo DuPont 11E") or ammonium salts such as, for example, ammonium sulphate or ammonium rhodanide.

The novel active compound combinations can be used as such, in the form of their formulations or in the use forms prepared therefrom by further dilution, such as ready-to-use solutions, suspensions, emulsions, powders, pastes and granules. They are applied in a customary manner, for example by watering, spraying, atomizing or broadcasting.

The application rates of the active compound combinations according to the invention can be varied within a certain range; they depend inter alia on the weather and on the soil factors. In general, the application rates are between 0.05 and 5 kg per ha, preferably between 0.05 and 2 kg per ha, particularly preferably between 0.1 and 1.0 kg per ha.

The active compound combinations according to the invention may be applied before and after the emergence of the plants, i.e. pre-emergence and post-emergence.

The good herbicidal action of the novel active compound combinations is evident from the examples which follow.

Whereas the individual active compounds have weaknesses in their herbicidal action, the combinations display throughout a very good action on weeds, which goes beyond simple summation of actions.

A synergistic effect is always present in herbicides when the herbicidal action of the active compound combination is greater than that of the individual active compounds applied.

The expected action of a given combination of two herbicides can be calculated as follows (cf. COLBY, S.R.: "Calculating synergistic and antagonistic responses of herbicide combinations", Weeds 15, pages 20–22, 1967):

If X = % damage by herbicide A (active compound of group 1) at an application rate of p kg/ha
and Y = % damage by herbicide B (active compound of group 2) at an application rate of q kg/ha and E = the expected damage of herbicides A and B at an application rate of p and q kg/ha, then E = X+Y-(X*Y/100).

If the actual damage is greater than calculated, then the combination is superadditive in its action; in other words, it exhibits a synergistic effect.

From the following examples it is evident that the herbicidal action of the active compound combinations according to the invention which has been found in weeds is greater than that calculated; in other words, that the novel active compound combinations act synergistically.

Use Examples

Pre-Emergence Test

Method 1
  Solvent: 5 parts by weight of acetone
  Emulsifier: 1 part by weight of alkylaryl polyglycol ether
  In order to produce a suitable preparation of active compound, 1 part by weight of a mixture of herbicidal active compound (herbicidal active compounds) and antidote/safener is mixed with the stated amount of solvent, the stated amount of emulsifier is added, and the concentrate is diluted with water to the desired concentration.

Method 2
  A quantity of antidote/safener corresponding to 0.2 % or another fraction of the weight of seed is shaken with the same weight of dextrin and 2 ml of methanol per 100 g of seed (maize) for several seconds, together with the seed, in disposable beakers. The methanol then evaporates within a few minutes at room temperature.

Active compounds, application rates and test results are evident from the tables below.

TABLE 1

Test on maize
Herbicide active compound of the formula (I): N-i-propyl-N-(4-fluoro-phenyl)-α-(5-trifluoromethyl-1,3,4,-imiadiazol-2-yl-oxy)-acetamide (I-1)
Antidote application according to method 1

| | Application rate (g/ha) | | % inhibition | | |
|---|---|---|---|---|---|
| Antidote | Herbicide | Antidote | Herbi-cide | Anti-dote | Herbicide + antidote |
| Furilazol | 1000 | 250 | 40 | 0 | 0 |
| (MON-13900) | 1000 | 100 | 40 | 0 | 0 |
| | 1000 | 50 | 40 | 0 | 0 |
| DKA-24 | 1000 | 250 | 40 | 0 | 0 |
| | 1000 | 100 | 40 | 0 | 0 |
| | 1000 | 50 | 40 | 0 | 0 |
| Dichlormid | 1000 | 250 | 40 | 0 | 0 |
| | 1000 | 100 | 40 | 0 | 0 |
| | 1000 | 50 | 40 | 0 | 0 |

TABLE 2

Test on maize
Herbicide active compound of the formula (I): N-i-propyl-N-(4-fluoro-phenyl)-α-(5-trifluoromethyl-1,3,4-thiadiazol-2-yl-oxy)-acetamide (I-1)
Antidote application according to method 2 (seed treatment)

| | Application rate (g/ha) | | % inhibition | | |
|---|---|---|---|---|---|
| Antidote | Herbicide (kg/ha) | (g/100 g seed) | Herbi-cide | Anti-dote | Herbicide + antidote |
| Furilazol | 1000 | 250 | 40 | 0 | 0 |
| (MON-13900) | 1000 | 50 | 40 | 0 | 0 |
| Dichlormid | 1000 | 250 | 40 | 0 | 0 |
| | 1000 | 50 | 40 | 0 | 0 |
| 1,8-Naphthalic | 1000 | 250 | 40 | 0 | 0 |
| anhydride | 1000 | 50 | 40 | 0 | 0 |

We claim:
1. Selective-herbicidal compositions, characterized by a content of an active compound combination consisting of
  (a) a heteroaryloxy-acetamide of the general formula (I)

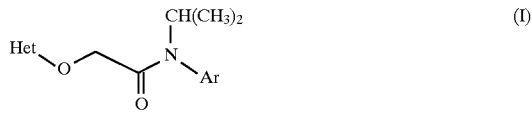

in which
  Het represents thiadiazolyl which is substituted by halogen or by $C_{1-C_4}$-alkyl or phenyl, each of which is optionally substituted by halogen, and
  Ar represents phenyl which is optionally substituted by halogen, $C_{1-C_4}$-alkyl or $C_{1-C_4}$-halogenoalkyl, ("active compounds of group 1") and
  (b) one or more compounds from a second group of herbicides which contains the active compounds mentioned below: N-(4,6-dimethoxy-pyrimidin-2-yl)-N'-(3-chloro-4-methoxycarbonyl-1-methyl-pyrazol-5-yl-sulfonyl)-urea(clopyrasulfuron, halosulfuron,NC-319), 2-chloro-N-(2,4-dimethyl-3-thienyl)-N-(2-methoxy-1-methyl-ethyl)-acetamide (dimethenamid, SAN-582),2-chloro-N-(2,6-dimethyl-phenyl)-N-(1H-pyrazol-1-yl-methyl)-acetamide (metazachlor), N-4,6-dimethoxy-pyrimidin-2-yl)-N'-(3-ethylsulfonyl-pyridin-2-yl-sulfonyl)-urea (rimsulfuron), 3-i-propyl-1H-2,1,3-benzothiadiazin-4(3H)-one (bentazone), 3,5-dibromo-4-hydroxy-benzonitrile (bromoxynil), 3,6-dichloro-2-methoxybenzoic acid (dicamba), 2,4-dichloro-phenoxyacetic acid (2,4-D), O-(6-chloro-3-phenyl-pyridazin-4-yl) S-octyl thiocarbonate(pyridate),(4-amino-3,5-dichloro-6-fluoro-pyridin-2-yl-oxy)-acetic acid (fluroxypyr), N-(2,6-difluoro-phenyl)-5-methyl-1, 2,4-triazolo[1,5-a]-pyrimidine-2-sulphonamide (flumetsulam, DE-498), N-(2,6-dichloro-3-methyl-phenyl)-5,7-dimethoxy-1,2,4-triazolo[1,5-a]-pyrimidine-2-sulphonamide (metosulam, DE-511),N-(4-methoxy-6-methyl-1,3,5-triazin-2-yl)-N-(2-(3,3,3-trifluoropropyl)-phenylsulphonyl)-urea(prosulfuron), 5-(N-(4-chloro-2-fluoro-5-methoxycarbonylmethylthio-phenyl)-imino)-tetrahydro-3-oxo-1H,3H-1,3,4-thiadiazolo[3,4-a]-pyridazine (KIH-9201), 2-(2-chloro-4-methylsulphonyl benzoyl) cyclohexane-1,3-dione (sulcotrione), N'-(4-(3,4-dihydro-2-methoxy-2,4,4-trimethyl-2H-1-benzopyran-7-yl-oxy)-phenyl)-N- methoxy-N-methyl-urea (metobenzuron, UMP-488),3-amino-2,5-dichloro-benzoic acid (chloramben),2-(2-chloro-phenyl-methyl)-4,4-dimethyl-isoxazolidin-3-one (clomazone), 2-(2,4-dichloro-5-methylsulphonylamino-phenyl)-4-difluoromethyl-5-methyl-2,4-dihydro-3H-1,2,4-triazol-3-one (sulfentrazone, F-6285),2-(4,5-dihydro-4-methyl -4-i-propyl-5-oxo-1H-imidazol-2-yl)-5-ethyl-pyridine-3-carboxylic acid (imazethapyr), 2-(4,5-dihydro-4-methyl-4-i-propyl-5-oxo-1H-imidazol-2-yl)-5-methyl-pyridine-3-carboxylic acid (imazamethapyr), 5-(2-chloro-4-trifluoromethyl-phenoxy)-2-nitro-benzoic acid ethoxycarbonylmethyl ester (fluoroglycofen-ethyl), 4-dipropylamino-3,5-dinitro-benzenesulphonamide (oryzalin),S-phenylmethylN,N-dipropyl-thiocarbamate(prosulfocarb),3-chloro-4-chloromethyl-1-(3-trifluoromethyl-phenyl)-pyrrolidin-2-one (fluorochloridone), 2-chloro-6-nitro-3-phenoxy-benzenamine (aclonifen), N'-(4-bromo-phenyl)-N -methoxy-N-methylurea (metobromuron), 9-hydroxy-9H-fluoren-9-carboxylic acid (flurenol),7-chloro-3-methyl-quinoline-8-carboxylic acid (quinmerac), 4-hydroxy-3,5-diiodo-benzonitrile (ioxynil), N-(3-(1-ethyl-1-methyl-propyl) -isoxazol-5-yl)-2,6-dimethoxy-benzamide (isoxaben), N'-(3-chloro-4-methoxy -phenyl)-N,N-dimethyl-urea (metoxuron), N-butyl-N'-(3,4-dichloro-phenyl)-N-methyl-urea (neburon),(4-chloro-2-methyl-phenoxy)-acetic acid (MCPA), 2-(4-chloro-2-methyl-phenoxy)-propionic acid (mecoprop),3,5-dibromo-4-hydroxy benzaldehyde O-(2,4-dinitro-phenyl) oxime (bromofenoxim), 4-chloro-2-oxo-3(2H)-benzothiazoleacetic acid (benazolin), 3,6-dichloro-pyridine-2-carboxylic acid (clopyralid), 2-(4-chloro-2-fluoro-5-(2-chloro-2-ethoxycarbonyl-ethyl) -phenyl)-4-difluoromethyl-5-methyl-2,4-dihydro-3H-1,2,4-triazol-3-one(F-8426), 1-(4-chloro-3-(2,2,3,3,3-pentafluoro-propoxymethyl)-phenyl)-5-phenyl-1H-1,2,4-triazole-3-carboxamide (flupoxam), 6-(6,7-dihydro-6,6-dimethyl-3H,5H-pyrrolo [2,1-c]-1,2,4-thiadiazol-3-ylideneamino)-7-fluoro-4-(2-propinyl)-2H-1,4benzoxazin-3-(4H)-one (thidiazimin), N-(4,6-dimethoxy-pyrimidin-2-yl)-N'-(2-cyclopropylcarbonyl-phenyl-sulphonyl)-urea (AC-322140), 4-chloro-3-(4-chloro -2-fluoro-5-ethoxycarbonyl-methoxy)-5-difluoromethoxy-1-methyl-pyrazole (ET-751), N-butoxymethyl-2-chloro-N-(2,6-diethyl-phenyl)-acetamide(butachlor),2-chloro-N-(2,6-diethyl-phenyl)-N-(2-propoxy-ethyl)-acetamide (pretilachlor), S-(phenylmethyl) N-ethyl-N-(1,2-dimethyl-propyl)-thiocarbamate (esprocarb), N-(4-methyl-phenyl)-N'-(1-methyl-1-phenyl-ethyl)-urea (dymron), 4-(2,4-dichloro-benzoyl)-1,3-dimethyl-5-(4-methyl-phenyl-sulphonyloxy)-pyrazole (pyrazolate), 4-(2,4-dichloro-benzoyl)-1,3-dimethyl-5-phenyl-carbonylmethoxy) -pyrazole(pyrazoxyfen), N-(4,6-dimethoxy-1,3,5-triazin-2-yl-N'-(2-(2-methoxy -ethoxy)-phenylsulphonyl)-urea (cinosulfuron), N-(4,6-dimethoxy-pyrimidin-2-yl)-N'- (4-ethoxycarbonyl-1-methyl-pyrazol-5-yl-sulphonyl)-urea (pyrazosulfuron -ethyl),N-4,6-dimethoxy-pyrimidin-2-yl)-N'-(2-chloro-imidazo[1,2-a]-pyridin-3-yl-sulphonyl-urea (imazosulfuron), S,S-dimethyl 2-difluoromethyl-4-i-butyl-6-trifluoromethyl-pyridine-3,5-dicarbothioate (dithiopyr),2-bromo-3,3-dimethyl-N -(1-methyl-1-phenyl-ethyl)-butanamide (bromobutide), 2-(2-naphthyloxy)-N -phenyl-propanamide (naproanilide), 2-chloro-N-(2,6-dimethyl-phenyl)-N-(3-methoxy-2-thienyl-methyl)-acetamide (thenylchlor), 1,3,5-trichloro-2-(4-nitro -phenoxy)-benzene (chlornitrofen) ,2,4-dichloro-1-(3-methoxy-4-nitro-phenoxy)-benzene (chlomethoxyfen) - ("active compounds of group 2") - and/or (c) a compound which improves the tolerance by crop plants, from the following group of compounds: a-(1, 3-dioxolan-2-yl-methoximino)-phenylacetonitrile (oxabetrinil), a-(cyanomethoximino)-phenylacetonitrile(cyometrinil),4-chloro-N-(1,3-dioxolan -2-yl-methoxy)-a-trifluoro-acetophenone oxime (fluxofenim), 4,6-dichloro-2-phenyl-pyrimidine (fenclorim), 4dichloroacetyl-3,4-dihydro-3-methyl-2H-1,4-benzoxazine(benoxacor),5-chloro-quinoxalin-8-oxy-acetic acid 1-methyl-hexyl -ester (cloquintocet), 2,2-dichloro-N-(2-oxo-2-(2-propenylamino)-ethyl)-N-(2 -propenyl)-acetamide (DKA-24), 1,8-naphthalic anhydride, 1-(2,4-dichloro -phenyl)-5-trichloromethyl-1H-1,2,4-triazole-3-carboxylic acid ethyl ester (fenchlorazol-ethyl), 2-chloro-4-trifluoromethyl-thiazole-5-carboxylic acid phenylmethyl ester (flurazole), 3-dichloroacetyl-5-(2-furanyl)-2,2-dimethyl -oxazolidine (furilazole, MON-13900), 4-dichloroacetyl-1-oxa-4-azaspiro[4.5]-decane (AD-67), 2-dichloromethyl-2-methyl-1,3-dioxolane (MG-191), 2,2-dichloro-N-(1,3-dioxolan-2-yl-methyl)-N-2-propenyl)-acetamide (PPG-1292), 2,2-dichloro-N,N-di-2-propenyl-acetamide (dichlormid),N-(4-methyl-phenyl)-N'-(1-methyl-1-phenyl-ethyl-urea (dymron), 1-dichloroacetyl-hexahydro-3,3,8a-trimethylpyrrolo[1, 2-a]-pyrimidin-6(2H)-one (BAS-14538), N-(2-methoxy -benzoyl)4-(methylaminocarbonylamino)-benzenesulphonamide-("antidotes" or ("safeners") from 0.001 to 1000 parts by weight of an active compound of group 2 and/or from 0.001 to 1000 parts by weight of one of the abovementioned antidotes/safeners being present per part by weight of an active compound of group 1 (i.e. of the formula (I)).

2. Selective-herbicidal compositions, characterized by a content of an active compound combination consisting of (a) a heteroaryloxy-acetamide of the general formula (I) according to claim 1, in which Het represents 1,2,4-thiadiazolyl or 1,3,4-thiadiazolyl, which is substituted by fluorine, chlorine, bromine or by methyl, ethyl, n- or i-propyl or phenyl, each of which is optionally substituted by fluorine and/or chlorine, and Ar represents phenyl which is optionally substituted by fluorine, chlorine, bromine, methyl or trifluoromethyl, ("active compounds of group 1") and (b) one or two compounds from a second group of herbicides which contains the active compounds mentioned below: N-(4,6-dimethoxy-pyrimidin-2-yl)-N'-(3-chloro-4-methoxycarbonyl-1-methyl pyrazol-5-yl-sulfonyl)-urea(clopyrasulfuron,halosulfuron,NC-319), 2-chloro-N (2,4-dimethyl-3-thienyl)-N-(2-methoxy-1-methyl-ethyl)-acetamide (dimethenamid, SAN-582),2-chloro-N-(2,6-dimethyl-phenyl)-N-(1H-pyrazol-1-yl-methyl)-acetamide (metazachlor), N-(4,6-dimethoxy-pyrimidin-2-yl)-N'-(3-ethylsulfonyl-pyridin-2-yl-sulfonyl)-urea (rimsulfuron), 3-i-propyl-1H-2,1,3-benzothiadiazin-4(3H)-one (bentazone), 3,5-dibromo-4-hydroxy-benzonitrile (bromoxynil), 3,6-dichloro-2-methoxybenzoic acid (dicamba), 2,4-dichloro -phenoxyacetic acid (2,4-D), O-(6-chloro-3-phenylpyridazin-4-yl) S-octyl thiocarbonate(pyridate),(4-amino-3,5-dichloro-6-fluoro-pyridin-2-yl-oxy)-acetic acid (fluroxypyr), N-(2,6-difluoro-phenyl)-5-methyl-1, 2,4-triazolo[1,5-a]-pyrimidine-2-sulphonamide (flumetsulam, DE498), N-(2,6-dichloro-3-methyl-phenyl)-5,7-dimethoxy-1,2,4-triazolo[1,5-a]-pyrimidine-2-sulphonamide (metosulam, DE-511), N-(4-methoxy-6-methyl-1,3,5-triazin-2-yl)-N'-(2-(3,3,3-trifluoropropyl)-phenylsulphonyl)-urea(prosulfuron), 5-(N-(4-chloro-2-fluoro-5-methoxycarbonylmethylthio-phenyl)-imino)-tetrahydro-3-oxo-1H,3H-1,3,4-thiadiazolo[3,4-a]-pyridazine (KIH-9201), 2-(2-chloro-4-methylsulphonyl-benzoyl) cyclohexane-1,3-dione (sulcotrione), N'-(4-(3,4-dihydro-2-methoxy 2,4,4-trimethyl-2H-1-benzopyran-7-yl-oxy)-phenyl)-N-methoxy-N-methyl-urea (metobenzuron, UMP-488),3-amino-2,5-dichloro-benzoic acid (chloramben),2-(2-chloro-phenyl-methyl)-4,4-dimethyl-isoxazolidin-3-one (clomazone), 2-(2,4-dichloro-5-methylsulphonylamino-phenyl)-4-difluoromethyl-5-methyl-2,4-dihydro-3H-1,2,4-triazol-3-one (sulfentrazone, F-6285),2-(4,5-dihydro-4-methyl-4-i-propyl-5-oxo-1H-imidazol-2-yl)-5-ethyl-pyridine-3-carboxylic acid (imazethapyr), 2-(4,5-dihydro-4-i-propyl-5-oxo-1H-imidazol-2-yl)-5-methyl-pyridine-3-carboxylic acid (imazamethapyr), 5-(2-chloro-4-trifluoromethyl-phenoxy)-2-nitro-benzoic acid ethoxycarbonylmethyl ester (fluoroglycofen-ethyl), 4-dipropylamino-3,5-dinitro-benzenesulphonamide (oryzalin),S-phenylmethylN,N-dipropyl-thiocarbamate (prosulfocarb),3-chloro -4-chloromethyl-1-(3-trifluoromethyl-phenyl)-pyrrolidin-2-one (fluorochloridone), -2-chloro -6-nitro-3-phenoxy-benzenamine (aclonifen), N'-(4-bromo-phenyl)-N-methoxy-N-methylurea (metobromuron), 9-hydroxy-9H-fluoren-9-carboxylic acid (flurenol), 7-chloro-3-methyl-quinoline-8-carboxylic acid (quinmerac), 4-hydroxy-3,5-diiodo-benzonitrile (ioxynil), N-(3-(1-ethyl-1-methyl-propyl) isoxazol-5-yl)-2,6-dimethoxy-benzamide (isoxaben), N'-(3-chloro-4methoxy-phenyl)-N,N-dimethyl-urea (metoxuron), N-butyl-N'-(3,4-dichloro-phenyl)-N -methyl-urea(neburon), (4-chloro-2-methyl-phenoxy)-acetic acid (MCPA),2-(4-chloro-2-methyl-phenoxy)-propionic acid (mecoprop),3,5-dibromo-4-hydroxy-benzaldehyde O-(2,4-dinitro-phenyl) oxime (bromofenoxim), 4-chloro-2-oxo 3(2H)-benzothiazoleacetic acid (benazolin), 3,6-dichloro-pyridine-2-carboxylic acid (clopyralid), 2-(4-chloro-2-fluoro-5-(2-chloro-2-ethoxycarbonyl-ethyl) -phenyl)-4-difluoromethyl-5-methyl-2,4-dihydro-3H-1,2,4-triazol-3-one(F-8426), 1-(4-chloro-3-(2,2,3,3,3-pentafluoro-propoxymethyl)-phenyl)-5-phenyl-1H-1,2,4-triazole-3-carboxamide (flupoxam), 6-(6,-dihydro-6,6-dimethyl-3H,5H pyrrolo [2,1-c]-1,2,4-thiadiazol-3-ylideneamino)-7-fluoro-4(2-propinyl)-2H-1,4-benzoxazin-3(4H)-one (thidiazimin), N-(4,6-dimethoxy-pyrimidin-2-yl)-N'-(2cyclopropylcarbonyl-phenyl-sulphonyl)-urea (AC-322140),4-chloro-3-(4-chloro 2-fluoro-5-ethoxycarbonyl-methoxy)-5-difluoromethoxy-1-methyl-pyrazole(ET-751), N-butoxymethyl-2-chloro-N-(2,6-diethyl-phenyl)-acetamide(butachlor),2chloro-N-(2,6-diethyl-phenyl)-N-(2-propoxy-ethyl)-acetamide (pretilachlor), S-(phenylmethyl) N-ethyl-N-(1,2-dimethyl-propyl)-thiocarbamate (esprocarb), N-(4-methyl-phenyl)-N'-(1-methyl-1-phenyl-ethyl)-urea (dymron), 4-(2,4-dichloro-benzoyl)-1,3-dimethyl-5-(4-methyl-phenyl-sulphonyloxy)-pyrazole (pyrazolate),4-(2,4-dichloro-benzoyl)-1,3-dimethyl-5-(phenyl-carbonylmethoxy) -pyrazole (pyrazoxyfen), N-(4,6-dimethoxy-1,3,5-triazin-2-yl)-N'-(2-(2-methoxy -ethoxy)-phenylsulphonyl)-urea (cinosulfuron), N-(4,6-dimethoxy-pyrimidin-2-yl)-N'-(4-ethoxycarbonyl-1-methyl-pyrazol-5-yl-sulphonyl)-urea (pyrazosulfuron-ethyl), N-(4,6-dimethoxy-pyrimidin-2-yl)-N'-(2-chloro-imidazo[1,2-a]-pyridin-3-yl-sulphonyl)-urea (imazosulfuron),S,S-dimethyl2-difluoromethyl-4-i-butyl-6-trifluoromethyl-pyridine-3, 5-dicarbothioate (dithiopyr),2-bromo-3,3-dimethyl-N-(1-methyl-1-phenyl-ethyl)-butanamide (bromobutide), 2-(2-naphthyloxy)-N- -phenyl-propanamide (naproanilide), 2-chloro-N-(2,6-dimethyl-phenyl)-N-(3-methoxy-2-thienyl-methyl)-acetamide (thenylchlor), 1,3,5-trichloro-2-(4-nitro-phenoxy)-benzene (chlornitrofen),2,4-dichloro-1-(3-methoxy-4-nitro-phenoxy)-benzene (chlomethoxyfen) - ("active compounds of group 2") - and/or (c) a compound which improves the tolerance by crop plants, from the following group of compounds: a-(1, 3-dioxolan-2-yl-methoximino)-phenylacetonitrile (oxabetrinil), a-(cyanomethoximino)-phenylacetonitrile (cyometrinil),4-chloro-N-(1,3-dioxolan -2-yl-methoxy)-a-trifluoro-acetophenone oxime (fluxofenim), 4,6-dichloro-2-phenyl-pyrimidine (fenclorim), dichloroacetyl-3,4-dihydro-3-methyl-2H-1,4-benzoxazine (benoxacor),5-chloro-quinoxalin-8-oxy-acetic acid 1-methyl-hexyl ester (cloquintocet), 2,2-dichloro-N-(2-oxo-2-(2-propenylamino)-ethyl)-N-(2propenyl)-acetamide (DKA-24), 1,8-naphthalic anhydride, 1-(2,4-dichloro phenyl)-5-trichloromethyl-1H-1,2,4-triazole-3-carboxylic acid ethyl ester (fenchlorazol-ethyl), 2-chloro-4-trifluoromethyl-thiazole-5-carboxylic acid phenylmethyl ester (flurazole), 3-dichloroacetyl-5-(2-furanyl)-2,2-dimethyl -oxazolidine (furilazole, MON-13900), 4-dichloroacetyl-1-oxa-azaspiro[4.5](AD-67), 2-dichloromethyl-2-methyl-1,3-dioxolane (MG-191), 2,2-dichloro-N-(1,3-dioxolan-2-yl-methyl)-N-(2-propenyl)-acetamide (PPG-1292), 2,2-dichloro-N,N-di-2-propenyl-acetamide (dichlormid),N-(4-methyl-phenyl)-N'-(1-methyl-1-phenyl-ethyl)-urea (dymron), 1-dichloroacetyl-hexahydro-3,3,8a-trimethylpyrrolo[1, 2-a]-pyrimidin-6(2H)-one (BAS-145138), N-(2-methoxy -benzoyl)-4-(methylaminocarbonylamino)-benzenesulphonamide - ("antidotes" or "safeners") -from 0.01 to 100 parts by weight of an active compound of group 2 and/or from 0.01 to 100 parts by weight of one of the abovementioned antidotes/safeners being present per part by weight of an active compound of group 1 (i.e. of the formula (I)).

3. Selective-herbicidal compositions, characterized by a content of an active compound combination consisting of (a) a heteroaryloxy-acetamide of the general formula (I) according to claim 1, in which Het represents 1,2,4-thiadiazolyl or 1,3,4-thiadiazolyl, which is substituted by chlorine, dichloromethyl, difluoromethyl, trichloromethyl, trifluoromethyl, chlorodifluoromethyl, fluorodichloromethyl or pentafluoroethyl, and Ar represents phenyl which is optionally substituted by fluorine, chlorine, methyl or trifluoromethyl, ("active compounds of group 1") and (b) one or two compounds from a second group of herbicides which contains the active compounds mentioned below: N-(4,6-dimethoxy-pyrimidin-2-yl)-N'-(3-chloro-4-methoxycarbonyl-1-methyl-pyrazol-5-yl-sulfonyl)-urea(clopyrasulfuron, halosulfuron,NC-319), 2-chloro-N (2,4-dimethyl-3-thienyl)-N-(2-methoxy-1-methyl-ethyl)-acetamide (dimethenamid,SAN-582),2-chloro-N-(2,6-dimethyl-phenyl)-N-(1H-pyrazol-1-yl-methyl-acetamide (metazachlor), N-(4,6-dimethoxy-pyrimidin-2-yl)-N'-(3-ethylsulfonyl-pyridin-2-yl-sulfonyl)-urea (rimsulfuron), 3-i-propyl-1H-2,1,3-benzothiadiazin-4(3H)-one (bentazone), 3,5-dibromo-4-hydroxy-benzonitrile (bromoxynil), 3,6-dichloro-2-methoxybenzoic acid (dicamba), 2,4-dichloro phenoxyacetic acid (2,4-D), O-(6-chloro-3-phenyl-pyridazin-4-yl) S-octyl thiocarbonate(pyridate),(4-amino-3,5-dichloro-6-fluoro-pyridin-2-yl-oxy)-acetic acid (fluroxypyr), N-(2,6-difluoro-phenyl)-5-methyl-1,2,4-triazolo[1,5-a]-pyrimidine-2-sulphonamide (flumetsulam, DE-498), N-(2,6-dichloro-3-methyl-phenyl)-5,7-dimethoxy-1,2,4-triazolo[1,5-a]-pyrimidine-2-sulphonamide (metosulam, DE-511), N-(4-methoxy-6-methyl-1,3,5-triazin-2-yl)-N'-(2-(3,3,3-trifluoropropyl)-phenylsulphonyl)-urea (prosulfuron) ,5-(N-(4-chloro-2-fluoro-5-methoxycarbonylmethylthio-phenyl)-imino)-tetrahydro-3-oxo-1H,3H- 1,3,4-thiadiazolo[3,4-a]-pyridazine (KIH-9201), 2-(2-chloro-4-methylsulphonyl -benzoyl)cyclohexane-1,3-dione (sulcotrione), N'-(4-(3,4-dihydro-2-methoxy -2,4,4-trimethyl-2H-1-benzopyran-7-yl-oxy)-phenyl)-N-methoxy-N-methyl-urea (metobenzuron,UMP-488),3-amino-2,5-dichloro-benzoic acid(chloramben), 2-(2-chloro-phenyl-methyl)-4,4-dimethyl-isoxazolidin-3-one (clomazone), 2-(2,4-dichloro-5-methylsulphonylamino-phenyl)-4-difluoromethyl-5-methyl-2,4-dihydro-3H-1,2,4-triazol-3-one (sulfentrazone, F-6285), 2-(4,5-dihydro-4-methyl 4-i-propyl-5-oxo-1H-imidazol-2-yl)-5-ethyl-pyridine-3-carboxylic acid (imazethapyr), 2-(4,5-dihydro-4-methyl-4-propyl-5-oxo-1H-imidazol-2-yl)-5-methyl-pyridine-3-carboxylic acid (imazamethapyr), 5-(2-chloro-4-trifluoromethyl-phenoxy)-2-nitro-benzoic acid ethoxycarbonylmethyl ester (fluoroglycofen-ethyl), 4-dipropylamino-3,5-dinitro-benzenesulphonamide (oryzalin),S-phenylmethylN,N-dipropyl-thiocarbamate(prosulfocarb),3-chloro 4-chloromethyl-1-(3-trifluoromethyl-phenyl)-pyrrolidin-2-one (fluorochloridone), 2-chloro-6-nitro-3-phenoxy-benzenamine (aclonifen), N'-(4-bromo-phenyl)-N -methoxy-N-methylurea (metobromuron), 9-hydroxy-9H-fluoren-9-carboxylic acid (flurenol), 7-chloro-3-methyl-quinoline-8-carboxylic acid (quinmerac), 4-hydroxy-3,5-diiodo-benzonitrile (ioxynil), N-(3-(1-ethyl-1-methyl-propyl) isoxazol-5-yl)-2,6-dimethoxy-benzamide (isoxaben), N'-(3-chloro-4-methoxy -phenyl)-N,N-dimethyl-urea (metoxuron), N-butyl-N'-(3,4-dichloro-phenyl)-N -methyl-urea (neburon), (4-chloro-2-methyl-phenoxy)-acetic acid (MCPA),2-(4-chloro-2-methyl-phenoxy)-propionic acid (mecoprop),3,5-dibromo-4-hydroxy-benzaldehyde O-(2,4-dinitro-phenyl) oxime (bromofenoxim), 4-chloro-2-oxo 3(2H)-benzothiazoleacetic acid (benazolin), 3,6-dichloro-pyridine-2-carboxylic acid (clopyralid), 2-(4-chloro-2-fluoro-5-(2-chloro-2-ethoxycarbonyl-ethyl) -phenyl)-4-difluoromethyl-5-methyl-2,4-dihydro-3H-1,2,4-triazol-3-one(F-8426), 1-(4-chloro-3-(2,2,3,3,3-pentafluoro-propoxymethyl)-phenyl)-5-phenyl-1H-1,2,4-triazole-3-carboxamide (flupoxam), 6-(6,7-dihydro-6,6-dimethyl-3H,5H-pyrrolo [2, 1-c]-1,2,4-thiadiazol-3-ylideneamino)-7-fluoro-4-(2-propinyl)-2H-1,4benzoxazin-3(4H)-one (thidiazimin), N-(4,6-dimethoxy-pyrimidin-2-yl)-N'-(2cyclopropylcarbonyl-phenyl-sulphonyl)-urea (AC-322140), 4-chloro-3-(4-chloro -2-fluoro-5-ethoxycarbonyl-methoxy)-5-difluoromethoxy-1-methyl-pyrazole(ET-751), N-butoxymethyl-2-chloro-N-(2,6-diethyl-phenyl)-acetamide (butachlor), 2-chloro-N-(2,6-diethyl-phenyl)-N-(2-propoxy-ethyl)-acetamide (pretilachlor), S-(phenylmethyl) N-ethyl-N-(1,2-dimethyl-propyl-thiocarbamate (esprocarb), N-(4-methyl-phenyl)-N'-(1-methyl-1-phenyl-ethyl-urea (dymron), 4(2,4-dichloro-benzoyl)-1,3-dimethyl-5-(4-methyl-phenyl-sulphonyloxy)-pyrazole (pyrazolate), 4-(2,4-dichloro-benzoyl)-1,3-dimethyl-5-(phenyl-carbonylmethoxy) -pyrazole (pyrazoxyfen),N-(4,6-dimethoxy-1,3,5-triazin-2-yl)-N'-(2-(2-methoxy -ethoxy)-phenylsulphonyl)-urea (cinosulfuron), N-(4,6-dimethoxy-pyrimidin-2-yl)-N'-(4-ethoxycarbonyl-1-methyl-pyrazol-5-yl-sulphonyl)-urea (pyrazosulfuron-ethyl), N-(4,6-dimethoxy-pyrimidin-2-yl)-N'-(2-chloro-imidazo[1,2-a]-pyridin-3-yl-sulphonyl)-urea (imazosulfuron), S,S-dimethyl 2-difluoromethyl-4-i-butyl-6-trifluoromethyl-pyridine-3,5-dicarbothioate (dithiopyr), 2-bromo-3,3-dimethyl-N -(1-methyl-1-phenyl-ethyl)-butanamide (bromobutide), 2-2-naphthyloxy)-N -phenyl-propanamide (naproanilide), 2-chloro-N-(2,6-dimethyl-phenyl)-N-(3-methoxy-2-thienyl-methyl)-acetamide (thenylchlor), 1,3,5-trichloro-2(4-nitro -phenoxy)-benzene(chlornitrofen), 2,4-dichloro-1-(3-methoxy-4-nitro-phenoxy) -benzene (chlomethoxyfen) - ("active compounds of group 2") - and/or (c) a compound which improves the tolerance by crop plants, from the following group of compounds: a-(1, 3-dioxolan-2-yl-methoximino)-phenylacetonitrile (oxabetrinil), a-(cyanomethoximino)-phenylacetonitrile(cyometrinil),4-chloro-N-(1,3-dioxolan -2-yl-methoxy)-a-trifluoro-acetophenone oxime (fluxofenim), 4,6-dichloro-2-phenyl-pyrimidine (fenclorim), 4-dichloroacetyl-3,4-dihydro-3-methyl-2H-1,4benzoxazine (benoxacor),5-chloro-quinoxalin-8-oxy-acetic acid 1-methyl-hexyl ester (cloquintocet), 2,2-dichloro-N-(2-oxo-2-(2-propenylamino)-ethyl)-N-(2-propenyl)-acetamide (DKA-24), 1,8-naphthalic anhydride, 1-(2,4-dichloro -phenyl)-5-trichloromethyl-1H-1,2,4-triazole-3-carboxylic acid ethyl ester (fenchlorazol-ethyl), 2-chloro-4-trifluoromethyl-thiazole-5-carboxylic acid phenylmethyl ester (flurazole), 3-dichloroacetyl-5-(2-furanyl)-2,2-dimethyl -oxazolidine (furilazole, MON-13900), 4-dichloroacetyl-1-oxa-4-azaspiro[4.5]decane (AD-67), 2-dichloromethyl-2-methyl-1,3-dioxolane (MG-191), 2,2-dichloro-N-(1,3-dioxolan-2-yl-methyl)-N-(2-propenyl)-acetamide (PPG-1292), 2,2-dichloro-N,N-di-2-propenyl-acetamide (dichlormid), N-(4-methyl-phenyl)-N'-(1-methyl-1-phenyl-ethyl)-urea (dymron), 1-dichloroacetyl-hexahydro-3,3,8a-trimethylpyrrolo[1, 2-a]-pyrimidin-6(2H)-one (BAS-145138), N-(2-methoxy -benzoyl)-4-(methylaminocarbonylamino)-benzenesulphonamide - ("antidotes" or "safeners") -from 0.1 to 10 parts by weight of an active compound of group 2 and/or from 0.1 to 10parts by weight of one of the abovementioned antidotes/safeners being present per part by weight of an active compound of group 1 (i.e. of the formula (I)).

4. Selective-herbicidal compositions, characterized by a content of an active compound combination consisting of
(a) a heteroaryloxy-acetamide of the general formula (I) according to claim 1, in which
Het represents 1,2,4-thiadiazolyl or 1,3,4-thiadiazolyl, which is substituted by chlorine, dichloromethyl, difluoromethyl, trichloromethyl, trifluoromethyl, chlorodifluoromethyl, fluorodichloromethyl or pentafluoroethyl, and
Ar represents phenyl which is optionally substituted by fluorine, chlorine, methyl or trifluoromethyl,
("active compounds of group 1") and
(b) one or two compounds from a second group of herbicides which contains the active compounds mentioned below: N-(4,6-dimethoxy-pyrimidin-2-yl)-N'-(3-chloro-4-methoxycarbonyl-1-methyl -pyrazol-5-yl-sulfonyl)-urea(clopyrasulfuron,halosulfuron,NC-319), 2-chloro-N -(2,4-dimethyl-3-thienyl)-N-(2-methoxy-1-methyl-ethyl)-acetamide (dimethenamid,SAN-582),2-chloro-N-(2,6-dimethyl-phenyl)-N-(1H-pyrazol-1 -yl-methyl-acetamide (metazachlor), N-(4,6-dimethoxy-pyrimidin-2-yl)-N'-(3-ethylsulfonyl-pyridin-2-yl-sulfonyl)-urea (rimsulfuron), 3-i-propyl-1H-2,1, 3benzotrhiadiazin-4(3H)-one (bentazone), 3,5-dibromo-4-hydroxy-benzonitrile bromoxynil 3,6-dichloro-2-methoxybenzoic acid (dicamba), 2,4-dichloro phenoxyacetic acid (2,4-D), O-(6-chloro-3-phenyl-pyridazin-4-yl) S-octyl thiocarbonate(pyridate) ,(4-amino-3,5-dichloro-6-fluoro-pyridin-2-yl-oxy)-acetic acid (fluroxypyr), N-(2,6-difluoro-phenyl)-5-methyl-1,2,4-triazolo[1,5-a]pyrimidine-2-sulphonamide (flumetsulam, DE498), N-(2,6-dichloro-3-methyl -phenyl)-5,7-dimethoxy- 1,2,4-triazolo[1,5-a]-pyrimidine-2-sulphonamide (metosulam, DE511), N-(4-methoxy-6-methyl-1,3,5-triazin-2-yl)-N'-(2-(3,3,3-trifluoropropyl-phenylsulphonyl)-urea(prosulfuron),5-(N-(4-chloro-2-fluoro-5-methoxycarbonylmethylthio-phenyl)-imino)-tetrahydro-3-oxo-1H,3H- 1,3,4-thiadiazolo[3,4-a]-pyridazine (KIH-9201), 2-(2-chloro-4-methylsulphonyl-benzoyl) cyclohexane-1,3-dione (sulcotrione), N'-(4-(3,4-dihydro-2-methoxy -2,4,4-trimethyl-2H-1-benzopyran-7-yl-oxy)-phenyl)-N-methoxy-N-methyl-urea (metobenzuron, UMP-488),3-amino-2,5-dichloro-benzoic acid (chloramben),2-(2-chloro-phenyl-methyl)-4,4-dimethyl-isoxazolidin-3-one (clomazone),2-(2,4-dichloro-5-methylsulphonylamino-phenyl)-4-difluoromethyl-5-methyl-2,4-dihydro-3H-1,2,4-triazol-3-one (sulfentrazone, F6285),2-(4,5,-dihydro-4-methyl -4-i-propyl-5-oxo-1H-imidazol-2-yl)-5-ethyl-pyridine-3-carboxylic acid (imazethapyr), 2-(4,5-dihydro-4-methyl-4-i-propyl-5-oxo-1H-imidazol-2-yl)-5methyl-pyridine-3-carboxylic acid (imazamethapyr), 5-(2-chloro-4-trifluoromethyl-phenoxy)-2-nitro-benzoic acid ethoxycarbonylmethyl ester (fluoroglycofen-ethyl), 4-dipropylamino-3,5-dinitro-benzenesulphonamide (oryzalin),S-phenylmethylN,N-dipropyl-thiocarbamate(prosulfocarb),3-chloro-4-chloromethyl-1-(3-trifluoromethyl-phenyl)-pyrrolidin-2-one (fluorochloridone), 2-chloro-6-nitro-3-phenoxy-benzenamine (aclonifen), N'-(4bromo-phenyl)-N -methoxy-N-methylurea (metobromuron), 9-hydroxy-9H-fluoren-9-carboxylic acid (flurenol), 7-chloro-3-methyl-quinoline-8-carboxylic acid (quinmerac), 4hydroxy-3,5-diiodo-benzonitrile (ioxynil), N-(3-(1-ethyl-1-methyl-propyl) -isoxazol-5-yl)-2,6-dimethoxy-benzamide (isoxaben), N'-(3-chloro-4-methoxy -phenyl)-N,N-dimethyl-urea (metoxuron), N-butyl-N'-(3,4-dichloro-phenyl)-N-methyl-urea (neburon), (4-chloro-2-methyl-phenoxy)-acetic acid MCPA), 2-(4 -chloro-2-methyl-phenoxy)-propionic acid (mecoprop), 3,5-dibromo-4-hydroxy -benzaldehyde O-(2,4-dinitro-phenyl oxime (bromofenoxim), 4-chloro-2-oxo- -3(2H)-benzothiazoleacetic acid (benazolin), 3,6-dichloro-pyridine-2-carboxylic acid (clopyralid), 2-(4-chloro-2-fluoro-5-(2-chloro-2-ethoxycarbonyl-ethyl) -phenyl)-4-difluoromethyl-5-methyl-2,4-dihydro-3H-1,2,4-triazol-3-(one(F-8426), 1-(4-chloro-3-(2,2,3,3,3,-pentafluoro-propoxymethyl)-phenyl-1H-1,2,4-triazole-3-carboxamide (flupoxam), 6-(6,7-dihydro-6,6-dimethyl-3H,5H-pyrrolo [2,1-c]-1,2,4-thiadiazol-3ylideneamino)-7-fluoro-4-(2-propinyl)-2H-1, 4benzoxazin-3(4H)-one (thiadiazimin), N-(4,6-dimethoxy-pyrimidin-2-yl)-N'-(2-cyclopropylcarbonyl-phenyl-sulphonyl)-urea (AC-322140), 4-chloro-3-(4-chloro 2-fluoro-5-ethoxycarbonyl-methoxy)-5-difluoromethoxy-1-methyl-pyrazole(ET-751), N-butoxymethyl-2-chloro-N-(2,6-diethyl-phenyl)-acetamide(butachlor),2-chloro-N-(2,6-diethyl-phenyl)-N-(2-propoxy-ethyl)-acetamide (pretilachlor), S-(phenylmethyl) N-ethyl-N-(1,2-dimethyl-propyl)-thiocarbamate (esprocarb), N-(4-methyl-phenyl)-N'-(1-methyl-1-phenyl-ethyl)-urea (dymron), 4-(2,4-dichloro-benzoyl)-1,3-dimethyl-5-(4-methyl-phenyl-sulphonyloxy)-pyrazole (pyrazolate), 4-(2,4-dichloro-benzoyl)-1,3-dimethyl-5-(phenyl-carbonylmethoxy)-pyrazole (pyrazoxyfen),N-(4,6-dimethoxy-1,3,5-triazin-2-yl)-N'-(2-(2-methoxy -ethoxy)-phenylsulphonyl)-urea (cinosulfuron), N-(4, 6-dimethoxy-pyrimidin-2-yl)-N'-(ethoxycarbonyl-1-methyl-pyrazol-5-yl-sulphonyl)-urea (pyrazosulfuron-ethyl), N-(4,6-dimethoxy-pyrimidin-2-yl)-N'-(2-chloro-imidazo[1,2-a]-pyridin-3-yl-sulphonyl)-urea (imazosulfuron), S.S-dimethyl 2-difluoromethyl-4-i-butyl-6-trifluoromethyl-pyridine-3,5-dicarbothioate (dithiopyr), 2-bromo-3,3-dimethyl-N -(1-methyl-1-phenyl-ethyl)-butanamide (bromobutide), 2-(2-naphthyloxy)-N-phenyl-propanamide (naproanilide), 2-chloro-N-(2,6-dimethyl-phenyl)-N-(3-methoxy-2-thienyl-methyl)-acetamide (thenylchlor), 1,3,5-trichloro-2-(4-nitro -phenoxy)-benzene (chlornitrofen) ,2,4-dichloro-1-(3-methoxy-4-nitro-phenoxy)-benzene (chlomethoxyfen) - ("active compounds of group 2").

5. Selective herbicidal compositions, characterized by a content of an active compound combination consisting of
(a) a heteroaryloxy-acetamide of the general formula (I) according to claim 1, in which
Het represents 1,2,4-thiadiazolyl or 1,3,4-thiadiazolyl, which is substituted by chlorine, dichloromethyl, difluoromethyl, trichloromethyl, trifluoromethyl, chlorodifluoromethyl, fluorodichloromethyl or pentafluoroethyl, and
Ar represents phenyl which is optionally substituted by fluorine, chlorine, methyl or trifluoromethyl,
("active compounds of group 1") and
(b) a compound which improves the tolerance by crop plants, from the following group of compounds: a -(1,3-dioxolan-2-yl-methoximino)-phenylacetonitrile (oxabetrinil), a-(cyanomethoximino)-phenylacetonitrile(cyometrinil),4-chloro-N-(1,3-dioxolan 2-yl-methoxy)-a-trifluoro-acetophenone oxime (fluxofenim), 4,6-dichloro-2-phenyl-pyrimidine (fenclorim), 4-dichloroacetyl-3,4-dihydro-3-methyl-2H-1,4benzoxazine (benoxacor), 5-chloro-quinoxalin-8-oxy-acetic acid 1-methyl-hexyl ester (cloquintocet), 2,2-dichloro-N-(2-oxo-2-(2-propenylamino)-ethyl)-N-(2-propenyl)-acetamide (DKA-24), 1,8-naphthalic anhydride, 1-(2,4-dichloro-phenyl)-5-trichloromethyl-1H-1,2,4-triazole-3-carboxylic acid ethyl ester (fenchlorazol-ethyl), 2-chloro-4-trifluoromethyl-thiazole-5-carboxylic acid phenylmethyl ester (flurazole), 3-dichloroacetyl-5-(2-furanyl)-2,2-dimethyl -oxazolidine (furilazole, MON-13900), 4-dichloroacetyl-1-oxa-4azaspiro[4.5]-decane (AD-67), 2-dichloromethyl-2-methyl-1,3-dioxolane (MG-191), 2,2-dichloro-N-(1,3-dioxolan-2-yl-methyl)-N-(2-propenyl)-acetamide (PPG-1292), 2,2-dichloro-N,N-di-2-propenyl-acetamide (dichlormid), N-(4-methyl-phenyl)-N'-(1-methyl-1-phenyl-ethyl)-urea (dymron), 1-dichloroacetyl-hexahydro-3,3,8a-trimethylpyrrolo[1,2-a]-pyrimidin-6(2H)-one (BAS-145138), N-(2-methoxy -benzoyl)-4-(methylaminocarbonylamino)-benzenesulphonamide - ("antidotes" or "safeners").

6. Selective-herbicidal compositions according to claim 4, characterized in that, in the active compound combinations, the weight ratio of the active compound of the formula (I) to the active compound/s of group 2 is between 1:0.01 and 1:100.

7. Selective-herbicidal compositions according to claim 5, characterized in that, in the active compound combinations, the weight ratio of active compound of the formula (I) to the antidote/safener is between 1:0.01 and 1:100.

8. Method for the selective combating of weeds, characterized in that an active compound combination according to claim 1 is allowed to act on weeds or their habitat.

9. The composition according to claim 1, wherein the active compound combination consists of (a) N-i-propyl-N-(4-fluoro-phenyl)-alpha-(5-trifluoromethyl- 1,3,4-thiadiazol-2-yl-oxy)-acetamide (I-1); and (b) N-(2,6-dichloro-3-methyl-phenyl)-5,7-dimethoxy-1,2,4-triazolo[1,5-a]-pyrimidine-2-sulphonamide (metosulam, DE 511).

* * * * *

UNITED STATES PATENT AND TRADEMARK OFFICE
CERTIFICATE OF CORRECTION

PATENT NO. : 5,858,920
DATED : January 12, 1999
INVENTOR(S) : Dahmen, et al.

It is certified that error appears in the above-identified patent and that said Letters Patent is hereby corrected as shown below:

| | |
|---|---|
| Col. 14, line 32 | Delete " $C_1$-$C_4$-alkyl " and substitute -- $C_1$-$C_4$-alkyl -- |
| Col. 14, line 35 | Delete " $C_1$-$C_4$-alkyl or C - -halogenoalkyl " and substitute -- $C_1$-$C_4$-alkyl or $C_1$-$C_4$-halogenoalkyl -- |
| Col. 14, line 45 | After " N- " insert -- ( -- |
| Col. 14, line 59 | Delete " -N- " and substitute -- -N'- -- |
| Col. 15, line 61 | After " N- " insert -- ( -- |
| Col. 15, line 62 | After " sulphonyl " insert -- ) -- |
| Col. 16, line 14 | Delete " 4dichloroacetyl- " and substitute -- 4-dichloroacetyl- -- |
| Col. 16, line 32 | Delete " (BAS-14538) " and substitute -- (BAS-145138) |
| Col. 17, line 5 | Delete " DE498 " and substitute -- DE-498 -- |
| Col. 17, line 25 | After " 4,5-dihydro- " insert -- 4-methyl -- |
| Col. 17, line 55 | After " 6-(6, " insert -- 7 -- |
| Col. 17, line 59 | Delete " (2cyclopropylcarbonyl " and substitute -- (2-cyclopropylcarbonyl -- |

UNITED STATES PATENT AND TRADEMARK OFFICE
CERTIFICATE OF CORRECTION

PATENT NO. : 5,858,920
DATED : January 12, 1999
INVENTOR(S) : Dahmen, et al.

Page 2 of 4

It is certified that error appears in the above-identified patent and that said Letters Patent is hereby corrected as shown below:

| | |
|---|---|
| Col. 18, line 29 | After " (fenclorim) " insert 4- -- |
| Col. 18, line 40 | After " [4.5] " insert -- decane -- |
| Col. 19, line 41 | After " methyl-4- " insert -- i -- |
| Col. 20, line 6 | Delete " 4benzoxazin " and substitute -- 4-benxoxazin -- |
| Col. 20, line 16 | After " 1-phenyl-ethyl " insert -- ) -- |
| Col. 20, line 46 | Delete " 4benzoxazine " and substitute -- 4-benzoxazine -- |
| Col. 20, last line | Delete " 10parts " and substitute -- 10 parts -- |
| Col. 21, line 25 | After " methyl " insert -- ) -- |
| Col. 21, line 28 | Delete " 3benxotrhiadiazin " and substitute -- 3- benzothiadiazin -- |
| Col. 21, line 36 | Delete " DE498 " and substitute -- D-498 -- |
| Col. 21, line 39 | Delete " DE511 " and substitute -- DE-511 -- |
| Col. 21, line 54 | Delete " F6285 " and substitute -- F-6285 -- |

UNITED STATES PATENT AND TRADEMARK OFFICE
CERTIFICATE OF CORRECTION

PATENT NO. : 5,858,920
DATED : January 12, 1999
INVENTOR(S) : Dahmen, et al.

It is certified that error appears in the above-identified patent and that said Letters Patent is hereby corrected as shown below:

| | |
|---|---|
| Col. 21, line 57 | Delete " 5methyl " and substitute -- 5-methyl -- |
| Col. 21, line 66 | Delete " (4bromo- " and substitute -- (4-bromo- -- |
| Col. 22, line 3 | Delete " 4hydroxy " and substitute -- 4-hydroxy -- |
| Col. 22, line 17 | After " triazol-3- " delete -- ( -- |
| Col. 22, line 18 | After " -phenyl " insert -- )-5-phenyl-- |
| Col. 22, line 21 | Delete " 3ylideneamino " and substitute -- 3-ylideneamino -- |
| Col. 22, line 22 | Delete " 4benzoxazin- " and substitute -- 4-benzoxazin- -- |

UNITED STATES PATENT AND TRADEMARK OFFICE
CERTIFICATE OF CORRECTION

PATENT NO. : 5,858,920

DATED : January 12, 1999

INVENTOR(S) : Dahmen, et al

It is certified that error appears in the above-identified patent and that said Letters Patent is hereby corrected as shown below:

Col. 23, line 7    Delete " 4benzoxazine " and substitute -- 4-benzoxazine --

Signed and Sealed this

Twenty-third Day of May, 2000

*Attest:*

*Attesting Officer*

Q. TODD DICKINSON

*Director of Patents and Trademarks*